(12) United States Patent
Sternberg et al.

(10) Patent No.: US 11,890,373 B2
(45) Date of Patent: Feb. 6, 2024

(54) INTRAVAGINAL DEVICE AND USES THEREOF

(71) Applicant: AQUAFIT INTIMATE LTD., Tel Aviv—Yafo (IL)

(72) Inventors: Rebecca Sternberg, Tel Aviv (IL); Vered Italiano, Kfar Ben Non (IL); Varda Messer, Tel Aviv (IL)

(73) Assignee: AQUAFIT INTIMATE LTD., Tel Aviv-Jaffa (IL)

(*) Notice: Subject to any disclaimer, the term of this patent is extended or adjusted under 35 U.S.C. 154(b) by 543 days.

(21) Appl. No.: 16/979,354

(22) PCT Filed: Mar. 11, 2019

(86) PCT No.: PCT/IL2019/050265
§ 371 (c)(1),
(2) Date: Sep. 9, 2020

(87) PCT Pub. No.: WO2019/175864
PCT Pub. Date: Sep. 19, 2019

(65) Prior Publication Data
US 2021/0000742 A1    Jan. 7, 2021

(30) Foreign Application Priority Data
Mar. 11, 2018  (IL) .......................... 258017

(51) Int. Cl.
| | | |
|---|---|---|
| *A61K 9/02* | (2006.01) | |
| *A61K 9/00* | (2006.01) | |
| *A61K 9/06* | (2006.01) | |
| *A61K 31/05* | (2006.01) | |
| *A61K 31/352* | (2006.01) | |
| *A61K 31/455* | (2006.01) | |
| *A61K 47/10* | (2017.01) | |
| *A61K 47/36* | (2006.01) | |
| *A61K 47/44* | (2017.01) | |

(52) U.S. Cl.
CPC ............ *A61K 9/0036* (2013.01); *A61K 9/025* (2013.01); *A61K 9/06* (2013.01); *A61K 31/05* (2013.01); *A61K 31/352* (2013.01); *A61K 31/455* (2013.01); *A61K 47/10* (2013.01); *A61K 47/36* (2013.01); *A61K 47/44* (2013.01)

(58) Field of Classification Search
CPC ........ A61K 9/0036; A61K 9/025; A61K 9/06; A61K 31/05; A61K 31/352; A61K 31/455; A61K 47/10; A61K 47/36; A61K 47/44; A61K 9/0031; A61K 9/0034; A61M 29/00; A61M 31/002; A61F 6/06; A61L 31/14; A61P 15/00
See application file for complete search history.

(56) References Cited

U.S. PATENT DOCUMENTS

| | | |
|---|---|---|
| 3,867,329 A | 2/1975 | Halpern |
| 4,211,769 A | 7/1980 | Okada |
| 4,480,642 A | 11/1984 | Stoy |
| 4,977,904 A | 12/1990 | Kaufman |
| 8,586,078 B2 | 11/2013 | Faure |
| 2002/0198136 A1 | 12/2002 | Mak |
| 2004/0009223 A1 | 1/2004 | Garg et al. |
| 2006/0286172 A1 | 12/2006 | Mahashabde |
| 2009/0088405 A1* | 4/2009 | Kehoe .................. A61K 9/0034 514/54 |
| 2011/0008266 A1 | 1/2011 | Tamarkin |
| 2013/0046275 A1 | 2/2013 | Holzer |
| 2015/0140113 A1 | 5/2015 | Jacobs et al. |
| 2015/0314035 A1 | 11/2015 | Rolfes Meyering |

FOREIGN PATENT DOCUMENTS

| | | |
|---|---|---|
| CN | 103528474 A | 1/2014 |
| EP | 1137409 B1 | 5/2004 |
| WO | 2016001911 A1 | 1/2016 |

OTHER PUBLICATIONS https://web.archive.org/web/20141108151133/https://www.cpkelco.com/products/gellan-gum/.*

Josef et al., (2010) Composite alginate hydrogels: An innovative approach for the controlled release of hydrophobic drugs. Acta Biomater 6(12): 4642-4649.

Singh et al., (2014) Guar gum and sesame oil based novel bigels for controlled drug delivery. Colloids Surf B Biointerfaces 123: 582-592.

Singh et al., (2014) Preparation and characterization of novel carbopol based bigels for topical delivery of metronidazole for the treatment of bacterial vaginosis. Mater Sci Eng C Mater Biol Appl 44: 151-158.

Cool Water Cones; dated May 1, 2017. Retrieved from: https://web.archive.org/web/20170501092036/https://www.coolwatercones.com/information-for-doctors.html on Sep. 14, 2020. 2 pages.

* cited by examiner

*Primary Examiner* — Jessica Worsham
(74) *Attorney, Agent, or Firm* — The Roy Gross Law Firm, LLC; Roy Gross

(57) ABSTRACT

The present invention relates to delivery devices adapted to mechanically dilate a pelvic anatomical canal, the delivery devices comprise a composition formulated as a gel comprising a beneficial or therapeutic agent, said delivery devices being capable of releasing the beneficial or therapeutic agent into the pelvic anatomical canal, specifically into the vaginal canal, and thereby treat vaginal conditions associated with vaginal narrowing, atrophy, or dryness.

18 Claims, 5 Drawing Sheets

INTRAVAGINAL DEVICE AND USES THEREOF

FIELD OF THE INVENTION

The present invention relates to delivery devices adapted to mechanically dilate a pelvic anatomical canal, the delivery devices comprise a composition formulated as a gel comprising a beneficial or therapeutic agent, said delivery devices being capable of releasing the beneficial or therapeutic agent into the pelvic anatomical canal, specifically into the vaginal canal, and thereby treat vaginal conditions associated with vaginal narrowing, atrophy, or dryness.

BACKGROUND OF THE INVENTION

Vaginal disorders or dysfunctions affect a large number (about 30%) of women and can have profound effects on quality of life. Many of the vaginal disorders are still poorly understood. As a consequence, treatments are often nonexistent, inefficient and/or invasive.

One example of a highly debilitating, vaginal disorder is dyspareunia. Dyspareunia is characterized by difficult or painful sexual intercourse, and it is caused by various medical and psychological problems. Some of the medical problems that can result in dyspareunia include vaginal stenosis and atrophy associated with aging or hormonal changes, radiation, transgender surgery, pelvic surgery, or with congenital abnormalities. Only partially effective or poorly effective symptomatic treatments, such as the use of lubricants, are typically employed.

Another poorly understood disorder is vulvodynia, which involves a number of syndromes, including vulvar vestibulitis, which is characterized by pain in the vulvar area. Vulvodynia also affects a woman's ability to have sexual intercourse. To date, only partially effective or poorly effective treatments that alleviate the symptoms of vulvodynia are available.

Another vaginal disorder is vaginismus which results from the involuntary spasm of the pelvic muscles surrounding the outer third of the vagina, and interferes with a woman's ability to have a sexual intercourse. Women suffering from vaginismus are sometimes even unable to undergo a routine gynecological examination. Typical treatments of vaginismus include, for example, psychological therapy and the use of a dilator to progressively release tension and muscle spasms of the contracted muscles of the vagina. Although often effective, these treatments cause high levels of anxiety.

U.S. Pat. No. 3,867,329 discloses compositions, article of manufacture, and a method for forming a hydrogel dilation device for internal use in the human body. According to U.S. Pat. No. 3,867,329, chemically actuated dilation devices, particularly cervical devices, are disclosed which are substantially moisture free and which absorb body fluid and swell, thereby causing cervical dilation. Among the hydrogel compositions disclosed, polyacrylamide gels, polyglyceryl monomethacrylate gels, polyvinyl alcohol gels or polyethylene glycol 4,000 diacrylate gels are listed.

U.S. Pat. No. 4,480,642 discloses a cervical canal swelling device having an essentially cylindrically shaped stem comprised of a dehydrated synthetic hydrogel having a swelling capacity of 0.01 to 0.25 and an enforced unimaxial deformation of at least 1.1. According to U.S. Pat. No. 4,480,642, the hydrogel is preferably derived from polyacrylonitrile and contains a major portion of acrylamide and acrylic acid units.

U.S. Pat. No. 4,977,904 discloses articles for the protection of humans, animals and other articles from damage due to undesired exposure to lasers comprising a tubular element comprising at least one layer comprising a xerogel, said xerogel comprising at least one water-insoluble hydrophilic polymer. According to U.S. Pat. No. 4,977,904, during surgery or therapy with lasers, the hydrophilic xerogels are hydrated by either water or aqueous solutions prior to, or after insertion of, the tubular element, so that the xerogels form hydrogels which protect the humans, animals and articles from the undesired exposure to the lasers. Such protective barriers include copolymers of acrylonitrile, acrylates or methacrylates with acrylamide, acrylic acid or methacrylic acid, which barriers can be used for surgical drapes, endotracheal tubes, and vaginal dilators, among others.

A dilator device named Cool Water Cones is currently commercially available. This device is made of a gel and contains more than 90% water and FDA approved natural ingredients, some of which are hydrocolloids.

Singh et al. (Materials Science and Engineering C 44: 151-158, 2014) disclosed bigels for topical delivery of metronidazole for the treatment of bacterial vaginosis. The bigels, containing sorbitan monostearate-sesame oil organogel loaded with metronidazole and carbopol 934 hydrogel, showed diffusion-mediated release of metronidazole and antimicrobial efficiency against *Escherichia coli*.

Singh et al. (Colloids and Surfaces B: Biointerfaces 123: 582-592, 2014) disclosed guar gum and sesame oil based bigels for topical drug delivery. The bigels containing guar gum hydrogel and sorbitan monostearate-sesame oil organogel loaded with ciprofloxacin released ciprofloxacin and showed antimicrobial efficiency against *Bacillus subtilis*.

Josef et al. (Acta Biomaterialia 6: 4642-4649, 2010) disclosed oil-in-water microemulsions in hydrophilic hydrogels for controlled release of hydrophobic drugs. According to Josef et al., a microemulsion which contained Tween 80, Span 20, and isopropyl myristate (IPM), and loaded with a hydrophobic drug, and an alginate gel which contained alginate, water, calcium ions and D(+)-gluconic acid δ-lactone (GDL), formed a clear hydrogel which released the hydrophobic drug in a release rate governed by the hydrogel properties and not by the microemulsion structure.

U.S. Pat. No. 8,586,078 discloses solid or semi-solid gels which comprise a hydrogel matrix and a hydrophobic oil dispersed within the hydrogel matrix, wherein the hydrogel matrix comprises water and a protein covalently cross-linked by a hydrophilic, gel-forming polymer. U.S. Pat. No. 8,586,078 further discloses a drug delivery device which comprises the solid or semi-solid gel and a biologically active agent.

There is still an unmet need for improved devices and methods for pain-free vaginal dilation.

SUMMARY OF THE INVENTION

The present invention provides delivery devices adapted to mechanically dilate an anatomical pelvic canal, specifically the vagina, and to deliver a beneficial or therapeutic agent into said anatomical pelvic canal. The present invention further provides methods for treating a woman suffering from any vaginal condition that requires vaginal dilation and lubrication. Additionally, the present invention provides methods for treating sexual dysfunction or improving female wellness and pleasure comprising inserting the delivery device of the present invention into the vaginal canal of a woman in need of such treatment, thereby treating female sexual dysfunction or improving female wellness and pleasure.

The present invention overcomes the drawbacks and disadvantages of known devices that are commonly prescribed or dispensed to women for use as vaginal dilators.

It is now disclosed that the delivery devices of the present invention which are formulated as a gel having a solid consistency are of sufficient rigidity to exert pressure on the vaginal walls yet are more elastic, pliable, and compressible than previous articles manufactured for the dilating purpose. The delivery devices of the present invention conform themselves more readily to the shape of the vaginal canal and thus provide better contact with the vaginal walls and greater comfort to the user. Consequently, the delivery devices of the present invention can efficiently dilate the vagina of women suffering from vaginal narrowing, such as women having vaginismus, dyspareunia, or vulvodynia.

It is further disclosed that due to the chemical nature of the constituents of the delivery devices of the present invention, specifically the naturally occurring polysaccharides which are generally recognized as safe (GRAS), the delivery devices of the present invention have self-lubrication effects, thus reducing discomfort, pain and/or injury during insertion of the devices into the vagina, and hence enhance compliance. The delivery devices of the present invention can therefore be easily and efficiently inserted by the woman in need of such treatment, obviating the need of assistance from a physician or from other health professional.

The delivery devices of the present invention maintain their shape over a range of temperatures and thus can conveniently be cooled or warmed due to their high water content to provide temperature therapy to the genital organs. The devices of the present invention can be warmed to relax vaginal, vulvar or pelvic muscle spasms. Alternatively, the devices can be cooled to induce anesthetic effects in the vaginal canal and to organs adjacent thereto.

The delivery devices of the present invention further comprise salts and acids, thus enabling the device to be biocompatible with the vaginal fluids and pH.

It is now disclosed that due to the constituents of the gel formulations of the present invention, specifically the presence of an oil-in-water emulsion prior to gelation/solidification, not only were the flexibility and elasticity of the devices improved, but the devices absorbed and released hydrophilic as well as hydrophobic active or beneficial agents. Thus, while in some embodiments, the device of the present invention is devoid of oil and is therefore a solid hydrogel, in other embodiments, the device of the present invention is a gel comprising an oil-in-water emulsion prior to solidification/gelation. While hydrogels can effectively release or deliver hydrophilic agents, gels comprising an oil-in-water emulsion prior to gelation/solidification can effectively release or deliver hydrophilic and/or hydrophobic agents. The present invention therefore provides easy to use vaginal dilators which also function as a delivery means for beneficial or therapeutic hydrophilic and/or hydrophobic agents to the vagina.

According to one aspect, the present invention provides a delivery device adapted to mechanically dilate a pelvic anatomical canal of a human subject, the delivery device comprises a composition comprising:
  (a) a naturally occurring polysaccharide;
  (b) water in an amount ranging from about 60% to about 88%, alternatively from 60% to 88%, by weight of the composition;
  (c) a surfactant in an amount ranging from 0% to about 5% by weight of the composition;
  (d) oil in an amount ranging from 0% to about 40% by weight of the composition;
  (e) a cross-linking agent; and
  (f) a hydrophilic agent and/or a hydrophobic agent, each having a beneficial or therapeutic effect in the pelvic anatomical canal,
  wherein the composition being formulated in the form of a gel.

According to some embodiments, the naturally occurring polysaccharide is selected from the group consisting of locust bean gum, carrageenan, gellan gum, agar, gum karaya, gum arabic, gum tragacanth, guar gum, konjac gum, pectin, xanthan gum, welan gum, native or modified starch, inulin, cellulose derivatives, chitin, chitosan, alginates, hyaluronic acid, and a combination thereof. Each possibility represents a separate embodiment of the invention. According to certain embodiments, the naturally occurring polysaccharide is locust bean gum, carrageenan, gellan gum, or a combination thereof.

According to additional embodiments, the amount of the naturally occurring polysaccharide(s) ranges from about 1% to about 5% by weight of the composition.

According to further embodiments, the surfactant is selected from the group consisting of nonionic surfactants, anionic surfactants, cationic surfactants, and amphoteric surfactants. Each possibility represents a separate embodiment of the invention. According to a certain embodiment, the surfactant is a nonionic surfactant.

According to yet further embodiments, the nonionic surfactant is selected from the group consisting of sorbitan fatty acid esters, polyoxysorbitan fatty acid esters, polyoxyalkylene higher alcohol ethers, polyoxyalkylene higher alcohol esters, and sucrose esters. According to still further embodiments, the nonionic surfactant is selected from the group consisting of polyoxyethylene sorbitol esters, polyoxyethylene isooctylphenyl ethers, polyoxyethylene nonylphenyl ethers, polyoxyethylene dodecyl ethers, octyl glucoside, and alkyl maltoside. According to yet further embodiments, the nonionic surfactant is selected from the group consisting of polysorbate 80 (TWEEN® 80), polysorbate 60 (TWEEN® 60), polysorbate 20 (TWEEN® 20), sucrose esters, glyceryl stearate, lecithin, polyglyceryl oleate, PEG-40 stearate, N-dodecyl-βD-maltoside, Triton X-100, Brij 58, Poloxamer 188, Tyloxapol, NP-40, Pluronic™ F-68, and Poloxamer 4070. Each possibility represents a separate embodiment of the invention. According to an exemplary embodiment, the nonionic surfactant is a combination of sucrose palmitate and sucrose distearate. According to some embodiments, the amount of the surfactant, preferably a nonionic surfactant, ranges from about 0.1% to about 5% by weight of the composition, alternatively from about 0.1% to about 3% by weight of the composition.

According to additional embodiments, the oil is a naturally occurring oil selected from the group consisting of a vegetable oil, an animal oil, and a mineral oil. According to further embodiments, the naturally occurring oil is a vegetable oil selected from the group consisting of coconut oil, corn oil, sesame seed oil, sunflower oil, walnut oil, canola oil, castor oil, olive oil, peanut oil, safflower oil, shia oil, and a mixture thereof. Each possibility represents a separate embodiment of the invention. According to some embodiments, the naturally occurring oil is present in an amount of up to about 40% by weight of the gel, alternatively the naturally occurring oil is present in an amount ranging from about 5% to about 30% by weight of the gel, or any integer in between, thus forming an oil-in-water emulsion prior to gelation when a surfactant is present.

According to additional embodiments, the cross-linking agent is selected from the group consisting of salts of monovalent cations, divalent cations, trivalent cations, quadrivalent cations, and a combination thereof. According to further embodiments, the cross-linking agent is a salt of a monovalent cation, a divalent cation, or a combination thereof. According to a certain embodiment, the cross-linking agent is a mixture of sodium chloride and potassium chloride or a mixture of calcium chloride and potassium chloride. According to some embodiments, the amount of the cross-linking agent is up to about 10% by weight of the composition. Alternatively, the amount of the cross-linking agent ranges from about 0.1% to about 5% by weight of the composition, or from about 0.1% to about 1%, or from 0.2% to about 0.5% by weight of the composition.

According to some embodiments, the gel is characterized by having Young's modulus of about 100 KPa to about 50 MPa. In some embodiments, the gel is characterized by having Young's modulus of about 100 KPa to about 10 MPa, alternatively of about 100 KPa to about 1.5 MPa, or of about 100 KPa to about 1 MPa. In certain embodiments, the gel is characterized by having Young's modulus of about 150 KPa to about 800 KPa, or of about 200 KPa to about 700 KPa.

According to additional embodiments, the hydrophilic agents and the hydrophobic agents are selected from the group consisting of vitamins, hyaluronic acid, collagen, *cannabis* oils, cannabinoids, probiotics, and plant extracts such as, but not limited to, hop extract, aloe vera extract, hemp extract, and jojoba oil. According to further embodiments, the hydrophilic agents and the hydrophobic agents are therapeutically active agents known to treat or affect a disease or a disorder of an anatomical pelvic canal, preferably the vagina.

According to still further embodiments, the vitamin is vitamin E, vitamin C, or a combination thereof.

According to yet further embodiments, the cannabinoid is selected from the group consisting of cannabidiol (CBD), tetrahydrocannabinol (THC) such as trans-$\Delta$9-tetrahydrocannabinol (THC-9) and trans-$\Delta$8-tetrahydrocannabinol (THC-8), cannabidiolic acid (CBDA), tetrahydrocannabinolic acid (THCA-A), cannabigerol (CBG), cannabinol (CBN), or a combination thereof According to still further embodiments, the therapeutically active agent is selected from the group consisting of antibacterial agents, antifungal agents, antiviral agents, analgesic agents, anti-itch agents, and anti-dryness or lubricating agents. Each possibility represents a separate embodiment of the invention.

According to additional embodiments, the composition further comprises one or more pharmaceutically acceptable excipients selected from the group consisting of polar co-solvents, pH modifying agents, stabilizers, and preservatives.

According to further embodiments, the polar co-solvent is selected from the group consisting of glycerol, polyethylene glycol (PEG), propylene glycol (PPG), hexylene glycol, diethylene glycol, polypropylene glycol, PPG n-alkanols, and (PPG) stearyl ether. Each possibility represents a separate embodiment of the invention. According to a certain embodiment, the polar co-solvent is glycerol. According to some embodiments, the polar co-solvent is present in the formulation in an amount of up to about 10% by weight of the composition.

According to still further embodiments, the pH modifying agents is an acid selected from the group consisting of citric acid, lactic acid, acetic acid, and phosphoric acid. Each possibility represents a separate embodiment of the invention. According to a certain embodiment, the pH modifying agent is citric acid.

According to some embodiments, the stabilizer is selected from the group consisting of trisodium citrate, glucose, mannose, and mannitol According to a certain embodiment, the stabilizer is trisodium citrate.

According to yet further embodiments, the preservative is selected from the group consisting of sodium benzoate, potassium sorbate, benzalkonium, trisodium citrate, and a combination thereof.

According to one exemplary embodiment, the pelvic anatomical canal is the vagina of a woman and the device is sized and configured for intra-vaginal insertion.

According to another exemplary embodiment, the pelvic anatomical canal is the anus of a human subject and the device is sized and configured for rectal insertion.

According to further embodiments, the pH of the composition ranges from about 3.5 to about 5. According to a certain embodiment, when the delivery device is adapted to be inserted into the vagina, the pH of the composition ranges from about 3.8 to about 4.2.

According to some embodiments, the device comprises a composition formulated as a gel, the composition comprising:
  (a) a naturally occurring polysaccharide in an amount ranging from about 1% to about 5% by weight of the composition;
  (b) water in an amount ranging ranges from about 60% to about 88% by weight of the composition;
  (c) a surfactant in an amount ranging from 0% to about 5% by weight of the composition;
  (d) oil in an amount ranging from 0% to about 40% by weight of the composition;
  (e) a cross-linking in an amount of up to about 10% by weight of the composition; optionally a polar co-solvent, and
  (f) a hydrophilic agent and/or a hydrophobic active agent.

According to additional embodiments, the device comprises a composition formulated as a hydrogel, the composition comprising:
  (a) a naturally occurring polysaccharide in an amount ranging from about 1% to about 5% by weight of the composition;
  (b) water in an amount ranging ranges from about 60% to 88% by weight of the composition;
  (c) a cross-linking agent in an amount ranging from 0.1% to about 5% by weight of the composition;
  (d) a polar co-solvent in an amount ranging from 0% to about 10% by weight of the composition; and
  (e) a hydrophilic agent and/or a hydrophobic active agent.

According to further embodiments, the device comprises a gel comprising an oil-in-water emulsion composition prior to gelation/solidification, which composition comprising:
  (a) a naturally occurring polysaccharide in an amount ranging from about 1% to about 5% by weight of the composition;
  (b) water in an amount ranging ranges from about 60% to about 88% by weight of the composition;
  (c) a surfactant in an amount ranging from about 0.1% to about 5% by weight of the composition;
  (d) oil in an amount ranging from 0.1% to about 40% by weight of the composition;

(e) a cross-linking agent in an amount ranging from 0.1% to about 5% by weight of the composition;
(f) a polar co-solvent in an amount ranging from 0% to about 10% by weight of the composition; and
(g) a hydrophilic agent and/or a hydrophobic agent.

According to yet further embodiments, the device comprises an oil-in-water emulsion composition prior to gelation/solidification, the composition comprising:
(a) a naturally occurring polysaccharide in an amount ranging from about 1% to about 5% by weight of the composition;
(b) water in an amount ranging ranges from about 60% to 88% by weight of the composition;
(c) a surfactant in an amount ranging from about 0.1% to about 3% by weight of the composition;
(d) oil in an amount ranging from 5% to about 30% by weight of the composition;
(e) a cross-linking agent in an amount ranging from 0.1% to about 1% by weight of the composition;
(f) a polar co-solvent in an amount ranging from 0% to about 10% by weight of the composition; and
(g) a hydrophilic agent and/or a hydrophobic agent.

According to another aspect, the present invention provides a method for relieving or treating pain and/or discomfort of a woman having a disorder selected from the group consisting of vaginal stenosis, vaginal adhesions, vaginal contractions and vaginal atrophy, the method comprising a step of inserting the delivery device of the present invention to the vaginal canal of the woman, thereby dilating the vaginal canal of said woman and relieving or treating the pain and/or discomfort of the woman Each possibility represents a separate embodiment of the invention.

According to some embodiments, the vaginal stenosis is associated with a disorder selected from the group consisting of dyspareunia, vulvodynia and vaginismus. Each possibility represents a separate embodiment of the invention. According to an additional embodiment, the vulvodynia is vulvar vestibulitis.

According to further embodiments, the vaginal stenosis or vaginal atrophy is due to menopause or to cancer therapy, e.g., radiation therapy.

According to another aspect, the present invention provides a method for treating female sexual dysfunction or for improving female sexual wellness and/or pleasure comprising a step of inserting the delivery device of the present invention to the vaginal canal of a woman in need of such treatment or improvement.

According to a further aspect, there is provided a delivery device according to the principles of the present invention for use in relieving or treating pain and/or discomfort of a woman having a disorder selected from the group consisting of vaginal stenosis, vaginal adhesions, vaginal contractions and vaginal atrophy.

According to another aspect, there is provided a delivery device according to the principles of the present invention for use in treating female sexual dysfunction or improving female sexual wellness and/or pleasure.

Each possibility disclosed throughout the application represents a separate embodiment of the invention.

BRIEF DESCRIPTION OF THE FIGURES

FIG. 1A is a perspective sectional view of an embodiment of a device of the present invention. FIG. 1B is a perspective side view of the device of FIG. 1A.

FIG. 3A shows the stress/strain curves of the gels 24 hrs after gel production. FIG. 3B shows the stress/strain curves of the gels one week after gel production.

DETAILED DESCRIPTION OF THE INVENTION

Figure 1A:
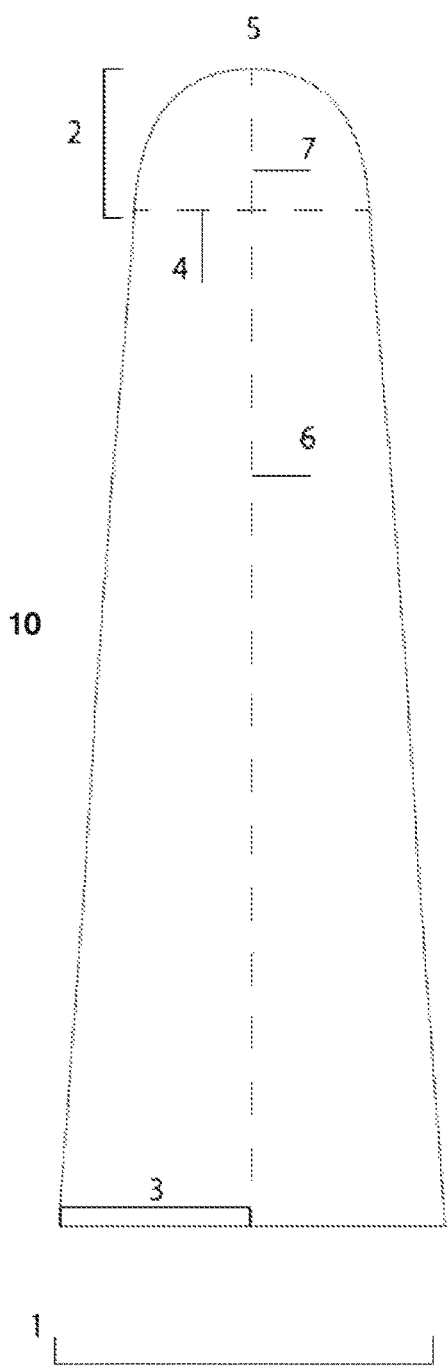
FIGS. 1A-B.

The present invention provides a delivery device adapted to be inserted into a pelvic anatomical canal of a human subject so as to dilate the pelvic anatomical canal. The device comprises a gel, preferably a hydrogel or a gel comprising an oil-in-water emulsion prior to gelation/solidification, which gel comprises a hydrophilic agent and/or a hydrophobic agent, each agent having a beneficial or therapeutic effect in the pelvic anatomical canal. The present invention further provides methods for vaginal dilation and/or for treating female sexual dysfunction and/or improving female sexual wellness comprising a step of inserting the delivery device of the present invention into the vagina of said woman, thereby dilating the vaginal canal.

Definitions

The term "delivery device" as used herein refers to a gel formulation that is contrived to deliver a desired agent, such as a vitamin, a cannabinoid, a lubricant, a drug, or a combination thereof. The delivery of one or more desired agents can be controlled so that the time of release, rate of release, and/or actual release and delivery of a desired agent may be preset by the composition of the device. Such control can occur by physical means and/or by chemical means. For example, the desired agent can be added to the composition prior to solidification, and/or the agent can be coated on the surface of the gel, and/or the gel can be impregnated in the agent solution, i.e., after solidification so as to control the release of a desired agent. Alternatively, the release of the desired agent can be controlled by the level of cross-linking of the polysaccharides which, in turn, depends on the amount of the polysaccharides in the composition, the amount and type of the cross-linking agents, etc.

The term "about" used throughout the specification and claims refers to ±10% of the indicated value.

The term "pharmaceutically acceptable" means approved by a regulatory agency of the Federal or a state government or listed in the U.S. Pharmacopeia or other generally recognized pharmacopeia for use in animals, and more particularly in humans Each and every constituent of the compositions of the present invention is a pharmaceutically acceptable agent.

The term "polar co-solvent" refers to an organic solvent, typically soluble in both water and oil.

The term "Young's modulus" as used herein, also known as "modulus of deformability", is a mechanical measure for evaluating the rigidity of gels which are not elastic. The modulus of deformability is derived from the slope of the initial straight line in the stress-strain curves.

The terms "gelation" and "solidification" are used interchangeably throughout the specification and claims to denote gel formation or polymerization, thus producing the gels of the invention.

The term "beneficial" effect as used herein refers to a lubricating effect in a pelvic anatomical canal and/or relaxation effect on pelvic muscles.

The term "therapeutically effective amount" is that amount of the active agent which is sufficient to provide a beneficial effect to the subject to which the active agent is administered. More specifically, a therapeutically effective amount means an amount of the active agent effective to alleviate or ameliorate the symptoms of a disorder of the subject being treated.

Devices and Methods of Preparation

The present invention provides a delivery device adapted to mechanically dilate a pelvic anatomical canal, the device comprising a composition formulated as a gel, the composition comprising:
  (a) a naturally occurring polysaccharide;
  (b) water in an amount ranging ranges from about 60% to about 88% by weight of the composition;
  (c) a pharmaceutically acceptable surfactant in an amount ranging from 0% to about 5% by weight of the composition;
  (d) a pharmaceutically acceptable oil in an amount ranging from 0% to about 40% by weight of the composition;
  (e) a pharmaceutically acceptable cross-linking agent; and
  (f) a hydrophilic agent and/or a hydrophobic active agent, each having a beneficial or therapeutic effect in the pelvic anatomical canal.

The naturally occurring polysaccharides useful for practicing the present invention include, but are not limited to, locust bean gum, carrageenan, gellan gum, agar, gum karaya, gum Arabic, gum tragacanth, guar gum, konjac gum, pectin, xanthan gum, welan gum, native or modified starch, inulin, cellulose derivatives such as, for example, hydroxypropyl cellulose, carboxymethyl cellulose, and hydroxyethyl cellulose, chitin, chitosan, alginates, and derivatives thereof. Hyaluronic acid is also encompassed for practicing the present invention. Each possibility represents a separate embodiment of the invention. According to the principles of the present invention, polysaccharides comprise or constitute the matrix or backbone of the gels of the present invention. However, in some embodiments, polysaccharides in combination with other natural occurring polymers, e.g., proteins, comprise or constitute the matrix or backbone of the gels of the present invention. Yet, proteins, e.g., collagen, can be used as beneficial or therapeutic agents.

According to a certain embodiment, the naturally occurring polysaccharide is selected from the group consisting of carrageenan, locust bean gum, gellan gum and a combination thereof. According to an exemplary embodiment, the naturally occurring polysaccharide is a combination of carrageenan, locust bean gum, and gellan gum.

The gel composition of the present invention comprises a pharmaceutically acceptable cross-linking agent. The pharmaceutically acceptable cross-linking agent is a salt of a monovalent cation or a multivalent cation such as a salt of a divalent cation, a trivalent cation or a tetravalent cation.

Examples of salts of monovalent cations include, but are not limited to, sodium chloride and potassium chloride. Examples of salts of divalent cations include, but are not limited to, calcium chloride, calcium sulfate, calcium phosphate, calcium carbonate, magnesium chloride, magnesium sulfate, magnesium phosphate, magnesium carbonate, manganese chloride, manganese sulfate, manganese phosphate, manganese carbonate, zinc chloride, zinc sulfate, zinc phosphate, and zinc carbonate. Examples of trivalent or tetravalent cations include, but are not limited to, $Al^{3+}$, $Fe^{3+}$, $Ce^{3+}$, $Sn^{4+}$, $Zr^{4+}$, and $Ti^{4+}$.

The device of the present invention can further comprise a pharmaceutically acceptable surfactant. A surfactant or a surface-active agent includes any agent linking oil and water in the composition, in the form of emulsion. A hydrophilic/lipophilic balance (HLB) of a surfactant indicates its affinity toward water or oil. The HLB scale ranges from 1 (totally lipophilic) to 20 (totally hydrophilic), with 10 representing an equal balance of both characteristics. Hydrophilic surfactants form oil-in-water (o/w) emulsions. The HLB of a blend of two emulsifiers equals the weight fraction of emulsifier A times its HLB value plus the weight fraction of emulsifier B times its HLB value (weighted average).

According to one or more embodiments of the present invention, the surface-active agent has a hydrophilic lipophilic balance (HLB) between about 3 and about 16, preferably between about 9 and about 14, which is the required HLB (the HLB required to stabilize an O/W emulsion of a given oil) of most oils and hydrophobic solvents. Thus, in one or more embodiments, the composition contains a single surface active agent having an HLB value between about 9 and 14, and in one or more embodiments, the composition contains more than one surface active agents and the weighted average of their HLB values is between about 9 and about 14.

Surfactants can be nonionic surfactants, anionic surfactants, cationic surfactants, and/or amphoteric surfactants.

Nonionic surfactants include, but are not limited to, sorbitan fatty acid esters, polyoxysorbitan fatty acid esters, polyoxyalkylene higher alcohol ethers, and polyoxyalkylene higher alcohol esters. Thus, nonionic surfactants include polyoxyethylene sorbitol esters such as polyoxyethylene sorbitan monolaurate (Tween 20), polyoxyethylene sorbitan monostearate (Tween 60) and polyoxyethylene sorbitan monooleate (Tween 80); Tyloxapol; polyoxyethylene isooctylphenyl ethers such as Triton X-100, poly(oxyethylene) nonylphenyl ethers such as NP-40, poly(oxyethylene) cetyl ether, poly(oxyethylene) palmityl ether; octyl glucoside, and alkyl maltoside such as n-dodecyl-beta-D-maltoside; Poloxamer 4070; Poloxamer 188; polyoxyl 40 stearate; glyceryl stearate; polyoxyethylene (POE) fatty acid esters, such as Myrj 45, Myrj 49, Myrj 52 and Myrj 59; poly(oxyethylene) alkylyl ethers, such as poly(oxyethylene) cetyl ether, poly(oxyethylene) palmityl ether, polyethylene oxide hexadecyl ether, poly(oxyethylene) dodecyl ethers such as Brij 58; polyethylene glycol cetyl ether; polyglyceryl oleate; lecithin; and any combination thereof. Each possibility is a separate embodiment of the invention. TWEEN® and poloxamer surfactants are preferred because they are FDA approved for human use.

Nonionic surfactants can also include, but are not limited to, fatty alcohol ethoxylates (alkylpolyethylene glycols); alkylphenol polyethylene glycols; alkylmercaptan polyethylene glycols; fatty amine ethoxylates (alkylaminopolyethylene glycols); fatty acid ethoxylates (acylpolyethylene glycols); polypropylene glycol ethoxylates (Pluronics™; e.g., Pluronic F-68); fatty acid alkylol amides, (fatty acid amide polyethylene glycols); N-alkyl-, N-alkoxypoly-hydroxy-fatty acid amide, sucrose esters; sorbitol esters and polyglycol ethers, polyoxyethylene-hydrogenated castor oil, fatty acid alkanolamide, sucrose fatty acid esters, glycerol mono, di- and trioctanoate. Each possibility is a separate embodiment of the invention.

Anionic surfactants include, but are not limited to, alkyl sulfates, olefin sulfates, ether sulfates, monoglyceride sulfates, alkyl sulfonates, aryl sulfonates, olefin sulfonates, alkyl sulfosuccinates, aryl sulfosuccinates, including sodium dodecyl sulphate (SDS), dioctyl sodium sulfosuccinate, dioctyl sodium sulfonate. Each possibility represents a separate embodiment of the invention.

Cationic surfactants include, but are not limited to, benzalkonium salts, polyoxyalkylene alkylamines, alkylamines, alkanolamine fatty acid esters, quaternary ammonium fatty acid esters, dialkyl ammonium salts, alkyl pyridinium salts including stearylamine, triethanolamine oleate, benzethonium chloride. Each possibility represents a separate embodiment of the invention.

Amphoteric surfactants include, for example, imidazoline-based amphoteric surfactants (such as a 2-cocoyl-2-imidazoliniumhydroxide-1-carboxyethyloxy-2-sodium salt), betaine-based surfactants (such as alkyl betaine, amide betaine, and sulfo betaine), and acylmethyl taurine. Each possibility represents a separate embodiment of the invention.

The naturally occurring oil can be a vegetable oil, an animal oil, or a mineral oil which can be used singly or in combination. Examples of vegetable or animal oils include, but are not limited to, *arachis* oil, castor oil, coconut oil, corn oil, canola oil, olive oil, peanut oil, safflower oil, soybean oil, sesame seed oil, rapeseed oil, sunflower oil, shia oil, flaxseed oil, walnut oil, fish oils, oils from marine planktons, and mixtures thereof. If the composition is devoid of the naturally occurring oil, the composition is a hydrogel. However, if the composition comprises surfactant(s) and naturally occurring oil(s), the composition is an oil-in-water emulsion. According to certain embodiments, the present invention provides devices which comprise an oil-in-water emulsion prior to gelation/solidification. By virtue of the oil-in-water emulsion prior to gelation, the devices of the present invention can deliver hydrophilic agents, hydrophobic agents, or a combination thereof.

Hydrophilic agents or hydrophobic agents which have a beneficial or therapeutic effect in the pelvic anatomical canal, e.g. vagina, include, but are not limited to, vitamins; probiotics; plant extracts such as extracts of Hop, aloe vera, Hemp, *Punica granatum, Acacia senegal, Andrographis paniculata, Curcuma comosa, Butea frondosa, Myristica fragrans, Asparagus racemosus, Butea monosperma, Acorus callomus;* cannabis oil and cannabinoids; lubricating agents, and drugs. Each possibility represents a separate embodiment of the invention.

Probiotics refer to a supplement which comprises viable bacteria and which improves or restores the vaginal flora. Any probiotics known in the art and suitable for vaginal application can be used. Probiotics typically include, but are not limited to, lactic acid producing bacteria, in particular genera of lactic acid bacteria, which have lactic acid as their main end product, such as selected strains of Lactobacilli, including *L. acidophilus, L. jensenii, L. gasseri, L. iners, L. delbrueckii, L. plantarum, L. crispatus, L. casei, L. fermenturn, L. reuterii, L. brevis, L. salivarius, L. johnsonii L. rhamnosus*; and selected strains of Bifidobacteria, including *B. bifidum, B. brevi, B. adolescentis* and *B. longum*, including mixtures of the mentioned strains. Other lactic acid producing bacteria which have been described as probiotics for vaginal application include species form *Bacillus*, such as *B. subtilis* and *B. coagulans*.

Drugs known to treat diseases, disorders, or dysfunction of a pelvic anatomical canal, particularly of the vagina, include, but are not limited to, antifungal agents such as nystatin, butoconazole, miconazole, fenticonazole, clotrimazole, tioconazole, terconazole, econazole, ketoconazole, sulconazole, candicidin, and the like; antibacterial agents such as clindamycin, tetracycline, amoxicillin, ampicillin, erythromycin, doxycycline, lumefloxacin, norfloxacin, afloxam, ciproflaxin, azitromycin, cefltoxine, and the like; antiviral agents such as acyclovir, femciclovir, valacyclovir, AZT, and the like; antiparasitic agents such as tinidazole, miconazole, metronidazole, secnidazole, and the like; steroids such as estradiol, progesterone, diethylstilbestrol, and the like; analgesic agents such as benzocaine, tetracaine, procaine, antipyrine, and the like; anti-itch agents such as capsaicin and its derivatives, e.g., nonivamide, corticosteroids, e.g., hydrocortisone and flurandrenolide, and herbal agents such as camomille, tea tree oil, calendula, and the like; and anti-dryness or lubricating agents such as hyaluronic acid, vitamin E, an estrogen, an aglycon isoflavone, collagen, plant hormones such as jasmonic acid and gibberellic acid, and a retinoid or carotenoid (e.g. vitamin A). Each possibility represents a separate embodiment of the invention.

Hydrophobic agents include, but are not limited to, certain steroids such as estradiol, progesterone, diethylstilbestrol, and the like; vitamins such as vitamin D, E, A, and K and water insoluble precursors and derivatives thereof; cannabinoids such as tetrahydrocannabinol, cannabidiol, and the like; hydrophobic antibiotics such as amphotericin B, adriamycin and the like. A hydrophobic biologically active agent can be dissolved in the hydrophobic/oil phase before or after emulsification and/or before or after gelation/solidification.

Hydrophilic agents include, but are not limited to, vitamin C and various known biologically or therapeutically active agents formulated as salts. Examples include lidocaine HCl, ephedrine sulfate, penicillin G sodium, and the like. A hydrophilic biologically or therapeutically active agent can be dissolved in the water or in the hydrophilic phase before or after emulsification and/or before or after gelation/solidification.

Hydrophobic and/or hydrophilic agents can be added to the device after gelation/solidification by surface coating of the gel, for example, by spraying a solution/dispersion of the agent. Alternatively or additionally, the hydrophobic and/or hydrophilic agents can be added to the device after gelation/solidification by deep coating, for example, by immersing the gel in a solution/dispersion of the agent.

The composition can further comprise one or more pharmaceutically acceptable excipients including, but not limited to, polar co-solvents, pH modifying agents, preservatives, and the like.

Examples of polar co-solvents include, but are not limited to, polyols, such as glycerol), propylene glycol (PPG), hexylene glycol, diethylene glycol, polypropylene glycol, PPG n-alkanols, and (PPG) stearyl ether. Each possibility represents a separate embodiment of the invention. According to a certain embodiment, the polar co-solvent is glycerol.

The pH modifying agents include, but are not limited to, lactic acid, acetic acid, citric acid, and phosphoric acid, to achieve the desired pH. Each possibility represents a separate embodiment of the invention. According to a certain embodiment, the pH modifying agent is citric acid.

The preservative can be any pharmaceutically acceptable preservative such as parabens, phenoxyethanol, salts of benzoic acid, sorbic acid or citric acid such as potassium sorbate, sodium benzoate or trisodium citrate, sodium metabisulfite, disodium EDTA, and chlorobutanol.

According to the principles of the present invention, all materials are pharmaceutically acceptable.

According to some embodiments, the composition is essentially devoid of proteins. The term "essentially devoid" refers to a composition containing less than 1% by weight of a protein, preferably less than 0.1% by weight of a protein, and more preferably less than 0.01% by weight of a protein. According to a certain embodiment, the composition is devoid of a protein.

If the device is being used for insertion into the vaginal canal, the pH of the composition prior to gelation/solidification ranges from about 3.0 to about 5.0, preferably the pH of the composition ranges from about 3.5 to about 5.0, and more preferably from about 3.8 to about 4.2.

The device of the present invention can adopt a variety of configurations. For example, the device can adopt a cone-like body such as a phallic-like shape having a proximal portion of a first diameter and a distal portion of a second diameter, wherein the first diameter is larger than the second diameter.

According to a preferred embodiment, the device of the present invention is integrally formed from a hydrogel or from an oil-in-water emulsion which then undergoes gelation/solidification. The device of the present invention is capable of producing a constant pressure to the pelvic anatomical canal walls, e.g., vaginal walls, during a treatment session so as to secure vaginal dilation sufficient to treat or ameliorate the pelvic pain syndrome. In addition, the device of the present invention is capable of making optimal or full contact with the vaginal canal. Thus, the device of the present invention can be useful as a means to prevent adhesions in an anatomical pelvic canal of a woman susceptible to such a condition. The device of the present invention can optionally provide heat or cold therapy, as desired.

Due to its close contact with the walls of the pelvic anatomical canal, fluids from the pelvic anatomical canal, e.g., vagina, can be absorbed by the device. Without being bound to any mechanism of action, such fluids can bring about the release of a hydrophilic or hydrophobic agent from the device.

According to some embodiments, the oil of the composition is solid at room temperature (~25° C.) but becomes liquid at body temperature. Such oil can be used in the delivery devices of the present invention for delivery of hydrophobic agents. Upon contact of the device with the walls of the pelvic anatomical canal, the oil-containing surface of the device undergoes phase change to a liquid, and the hydrophobic agent can be released. Thus, the delivery device of the present invention can efficiently deliver the desired agent to the vagina, specifically localizing it adjacent to the vaginal walls, hence improving the beneficial or therapeutic efficacy of the desired agent.

According to some embodiments, the release of the desired agent from the delivery device occurs within seconds up to two hours after insertion of the device into the pelvic anatomical canal. Alternatively, the release of the desired agent occurs within 30 minutes, 20 minutes, 15 minutes, or within 10 minutes, or any integer in between after insertion of the device into the pelvic anatomical canal. According to a certain embodiment, the delivery device is inserted into the vagina of a woman for a period of time of about 1 to 30 minutes, alternatively for a period of about 2 to 20 minutes, for a period of about 3 to 15 minutes or for a period of 5 to 10 minutes, during which the desired agent is released in an amount which is capable of exerting a beneficial or therapeutic effect in the vagina of the treated woman.

The device of the present invention can be either straight or curved, wherein if curved it has a curvature or a bend so as to facilitate positioning and manipulation of the device during use. According to one embodiment, the device has a curvature or a bend from the midline to the distal portion of the device of about 0-9°. According to a certain embodiment, the device has a curvature or a bend from the midline to the distal portion of the device of about 7°. Such bent configuration makes it easier for patients to self-insert the device in a pain-free manner without the need of assistance from another person.

According to some embodiments, the diameter of the proximal portion ranges from about 20 mm to about 60 mm, the diameter of the distal portion ranges from about 10 mm to about 30 mm, the length of the device ranges from about 120 mm to about 170 mm, and the length of the distal portion ranges from about 10 mm to about 20 mm.

Device 10, an embodiment of the device of the present invention, is depicted in FIG. 1A. The device 10 comprises a proximal portion 1 and a distal portion 2. The diameter 3 of the proximal portion 1 is of about 50 mm, the diameter 4 of the distal portion 2 is of about 30.5 mm. The distal portion 2 has a smooth-contoured close-end 5. The length 6 of the device is of about 15 cm, the length 7 of the distal portion is of about 1.9 cm.

Figure 1B:
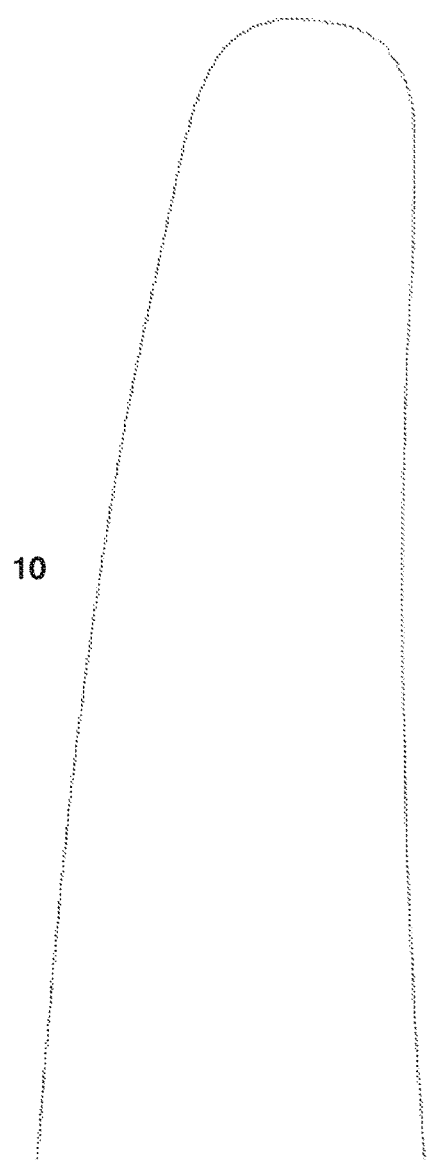

A side view of device 10 is depicted in FIG. 1B. The device 10 has a curvature or a bend of 9° at the distal portion.

The device of the present invention is suitable for delivering cold/heat therapy into the vagina in addition to pressure therapy. Due to its chemical constituents, the device of the invention is sufficiently rigid so as to provide significant pressure onto the pelvic anatomical canal walls, e.g., vaginal walls, as well as sufficiently flexible and lubricated to be easily inserted into the pelvic anatomical canal, e.g., vagina, causing minor or even no pain. Additionally, due to its high water content, the device can be easily heated or cooled to a treatment temperature and retain and transmit the heat or cold to the tissue during therapy.

The devices of the present invention are characterized mechanically by measuring their stiffness or rigidity, i.e., Young's modulus, also defined as modulus of deformability or compression modulus. Like the modulus of elasticity, the modulus of deformability is derived from the slope of the initial straight line in the stress-strain curves. The stress-strain data of the present invention were obtained in a compression assay using Instron 3345 Tester equipped with a 100 N load cell, and using a crosshead speed of 2 mm/min at a temperature of 22° C.

According to some embodiments, the delivery device of the present invention is characterized by having a compressive strain at break of at least 10% under a corrected stress of about 0.1 MPa. The compressive strain at break was determined in a compression assay using Instron 3345 Tester equipped with a 100 N load cell, and using a crosshead speed of 2 mm/min at ambient temperature. According to further embodiments, the delivery device is characterized by having a compressive strain at break of at least 20%, alternatively of at least 30%, at least 40%, or at least 50% of the gel's dimensions, i.e., cross-section or diameter, prior to compression. Each possibility represents a separate embodiment of the invention. In other words, under these compression conditions, the device undergoes enlargement of its cross-section or diameter as measured in millimeters of at least 10%, at least 20%, at least 30%, at least 40% or at least 50%, as compared to its cross-section or diameter prior to compression.

According to additional embodiments, the delivery device is characterized by having a compression modulus or Young's modulus of at least 0.1 MPa. According to some embodiments, the gel, which is also defined as a solid gel, is characterized by having Young's modulus of about 100 KPa to about 50 MPa. In some embodiments, the solid gel is characterized by having Young's modulus of about 100 KPa to about 10 MPa, or of about 100 KPa to about 1.5 MPa. In some embodiments, the solid gel is characterized by having Young's modulus of about 100 KPa to about 1 MPa, or of about 150 KPa to about 800 KPa, or of about 200 KPa to about 700 KPa, or any integer in between. Each possibility represents a separate embodiment of the invention.

According to some embodiments, the device comprises a composition formulated as a gel, the composition comprising:
  (a) a naturally occurring polysaccharide in an amount ranging from about 1% to about 5% by weight of the composition;
  (b) water in an amount ranging ranges from about 60% to about 88% by weight of the composition;
  (c) a surfactant in an amount ranging from about 0% to about 5% by weight of the composition;
  (d) oil in an amount ranging from 0% to about 40% by weight of the composition;
  (e) a cross-linking in an amount of up to about 10% by weight of the composition; optionally a polar co-solvent, and
  (f) a hydrophilic agent and/or a hydrophobic active agent.

According to additional embodiments, the device comprises a composition formulated as a hydrogel, the composition comprising:
  (a) a naturally occurring polysaccharide in an amount ranging from about 1% to about 5% by weight of the composition;
  (b) water in an amount ranging ranges from about 60% to 88% by weight of the gel;
  (c) a cross-linking agent in an amount ranging from 0.1% to about 5% by weight of the composition;
  (d) a polar co-solvent in an amount ranging from 0% to about 10% by weight of the composition; and
  (e) a hydrophilic agent and/or a hydrophobic active agent.

According to further embodiments, the device comprises a gel comprising an oil-in-water emulsion composition prior to gelation/solidification, which composition comprising:
  (a) a naturally occurring polysaccharide in an amount ranging from about 1% to about 5% by weight of the composition;
  (b) water in an amount ranging ranges from about 60% to about 88% by weight of the composition;
  (c) a surfactant, preferably a nonionic surfactant, in an amount ranging from about 0.1% to about 5% by weight of the composition;
  (d) oil, preferably a vegetable oil, in an amount ranging from 0.1% to about 40% by weight of the composition;
  (e) a cross-linking agent in an amount ranging from 0.1% to about 5% by weight of the composition;
  (f) a polar co-solvent in an amount ranging from 0% to about 10% by weight of the composition; and
  (g) a hydrophilic agent and/or a hydrophobic agent.

According to yet further embodiments, the device comprises an oil-in-water emulsion composition prior to gelation/solidification, the composition comprising:
  (a) a naturally occurring polysaccharide in an amount ranging from about 1% to about 5% by weight of the composition;
  (b) water in an amount ranging ranges from about 60% to 88% by weight of the composition;
  (c) a surfactant, preferably a nonionic surfactant, in an amount ranging from about 0.1% to about 3% by weight of the composition;
  (d) oil, preferably a vegetable oil, in an amount ranging from 5% to about 30% by weight of the composition;
  (e) a cross-linking agent in an amount ranging from 0.1% to about 1% by weight of the composition;
  (f) a polar co-solvent in an amount ranging from 0% to about 10% by weight of the composition; and
  (g) a hydrophilic agent and/or a hydrophobic agent.

According to some embodiments, the delivery device comprises a composition comprising:
  (a) a naturally occurring polysaccharide selected from the group consisting of locust bean gum, carrageenan, gellan gum, agar, gum karaya, gum arabic, gum tragacanth, guar gum, konjac gum, pectin, xanthan gum, welan gum, native or modified starch, inulin, cellulose derivatives, chitin, chitosan, and alginates or a combination thereof;
  (b) water in an amount of about 60% to 88% by weight of the composition;
  (c) a nonionic surfactant in an amount of 0% to about 5% by weight of the composition;
  (d) a naturally occurring vegetable oil selected from the group consisting of coconut oil, canola oil, almond oil, castor oil, corn oil, olive oil, peanut oil, safflower oil, shia oil, soybean oil, sesame seed oil, sunflower oil, and walnut oil, or mixtures thereof in an amount of 0% to about 40% by weight of the composition;
  (e) a cross-linking agent; and
  (f) a hydrophilic agent and/or a hydrophobic agent, each having a beneficial or therapeutic effect in the pelvic anatomical canal,
  wherein the composition being formulated in the form of a gel.

According to additional embodiments, the delivery device comprises an oil-in-water emulsion composition prior to gelation/solidification which comprises:
  (a) a naturally occurring polysaccharide selected from the group consisting of locust bean gum, carrageenan, gellan gum, agar, gum karaya, gum arabic, gum tragacanth, guar gum, konjac gum, pectin, xanthan gum, welan gum, native or modified starch, inulin, cellulose derivatives, chitin, chitosan, and alginates or a combination thereof;
  (b) water in an amount of about 60% to 88% by weight of the composition;
  (c) a nonionic surfactant in an amount of 0.1% to about 5% by weight of the composition;
  (d) a vegetable oil selected from the group consisting of coconut oil, canola oil, almond oil, castor oil, corn oil, olive oil, peanut oil, safflower oil, shia oil, soybean oil, sesame seed oil, sunflower oil, and walnut oil, or mixtures thereof in an amount of up to about 40% by weight of the composition;
  (e) a cross-linking agent; and
  (f) a hydrophilic agent and/or a hydrophobic agent, each having a beneficial or therapeutic effect in the pelvic anatomical canal, wherein the composition being formulated in the form of a gel.

According to yet further embodiments, the delivery device comprises an oil-in-water emulsion composition prior to gelation/solidification which comprises:
- (a) a naturally occurring polysaccharide selected from the group consisting of locust bean gum, carrageenan, gellan gum, agar, gum karaya, gum arabic, gum tragacanth, guar gum, konjac gum, pectin, xanthan gum, welan gum, native or modified starch, inulin, cellulose derivatives, chitin, chitosan, and alginates or a combination thereof in an amount ranging from about 1% to about 5% by weight of the composition;
- (b) water in an amount ranging from about 60% to about 80% by weight of the composition;
- (c) a nonionic surfactant in an amount ranging from about 0.1% to about 3% by weight of the composition;
- (d) a vegetable oil selected from the group consisting of coconut oil, canola oil, almond oil, castor oil, corn oil, olive oil, peanut oil, safflower oil, shia oil, soybean oil, sesame seed oil, sunflower oil, and walnut oil, or mixtures thereof in an amount ranging from about 5% to about 30% by weight of the composition;
- (e) glycerol in an amount ranging from about 0% to about 5% by weight of the composition;
- (f) a salt of a monovalent and/or a divalent cation in an amount of up to about 10% by weight of the composition;
- (g) a pH modifying agent; and
- (h) a hydrophilic agent and/or a hydrophobic agent, each having a beneficial or therapeutic effect in the pelvic anatomical canal.

According to still further embodiments, the delivery device comprises an oil-in-water emulsion composition prior to gelation/solidification which comprises:
- (a) locust bean gum, carrageenan, and gellan gum in an amount ranging from about 1% to about 5% by weight of the composition;
- (b) water in an amount ranging from about 60% to about 80% by weight of the composition;
- (c) a nonionic surfactant, preferably one or more sucrose esters, in an amount ranging from about 0.1% to about 3% by weight of the composition;
- (d) a vegetable oil, preferably coconut oil, in an amount ranging from about 5% to about 30% by weight of the composition;
- (e) glycerol in an amount ranging from about 0% to about 5% by weight of the composition;
- (f) a salt of a monovalent and/or a divalent cation in an amount ranging from about 0.1% to about 5% by weight of the composition;
- (g) a pH modifying agent; and
- (h) a hydrophilic agent and/or a hydrophobic agent, each having a beneficial or therapeutic effect in the pelvic anatomical canal.

Uses of the Device

The present invention provides methods for dilating a pelvic anatomical canal as well as delivering thereto a desired agent comprising inserting the delivery device of the present invention into the subject's pelvic anatomical canal, thereby dilating said pelvic anatomical canal and delivering the desired agent thereto. According to e certain embodiment, the pelvic anatomical canal is the vaginal canal.

According to one aspect, the present invention provides methods for treating a vaginal disorder or dysfunction comprising inserting the delivery device of the present invention into the vaginal canal of a woman at risk of having or having vaginal disorder or dysfunction, thereby treating the vaginal disorder or dysfunction. Examples of vaginal disorders or dysfunction that can be treated by the delivery device of the present invention include vaginal stenosis, vaginal adhesions, vaginal contractions, vaginal atrophy, and vaginal dryness.

The present invention further provides methods for relieving or treating pain and/or discomfort in a woman having a disorder selected from the group consisting of dyspareunia, vulvodynia or vaginismus comprising inserting the delivery device of the present invention to the vaginal canal of said woman for one or more treatment sessions, thereby dilating the vaginal canal and delivering an active agent such as an analgesic agent so as to relieve or treat the pain associated with said disorder.

The device of the present invention predominantly provides pressure on the pelvic anatomical canal walls, e.g., vaginal walls or cervical walls, so as to stretch and increase the canal cavity, e.g., vaginal cavity or cervical canal. The device of the present invention may also provide temperature therapy.

According to some embodiments of the present invention, one can induce an anesthetic effect in the pelvic region by using the delivery device of the invention to provide cold therapy via the vaginal cavity. Alternatively, one may relax muscles by using the delivery device according to the invention to provide heat therapy via the vaginal cavity.

As the delivery device of the present invention comprises one or more active agents, the delivery device can provide an analgesic effect, can treat bacterial and/or fungal and/or yeast and/or viral infections, and/or can reduce or eliminate muscle contractions.

The methods of the present invention relieve or treat pain due to a pelvic disorder selected from the group consisting of: painful intercourse or dyspareunia, vaginismus (spasming of the muscles at the opening of the vagina), vulvodynia, spasms of the pelvic floor muscles, myofascial pain syndrome, interstitial cystitis (a syndrome that may include suprapubic pain present in the lower abdomen, perineal pain present between the vagina and anus, pain during sexual intercourse), or chronic pelvic pain (including pressure or heaviness deep within the pelvis independent of or associated with intercourse, bowel movements, or sitting).

Pain can be associated with or resulting from complications following gynecological cancer treatments, for example, surgery or radiation therapy. Side effects of cancer treatment on genital organs, e.g., vagina, can make resuming sex more painful or difficult.

The delivery device of the present invention can also be useful for sex aid and/or for sex training and/or for lubricating the vaginal canal and/or for relaxation of pelvic muscles. Thus, the device of the present invention can treat or alleviate sexual dysfunction and/or increase sexual pleasure and/or relieve vaginal examination.

The device of the present invention can also be sized and configured for rectal insertion.

The compositions of the present invention comprise a hydrophilic or a hydrophobic agent as an active agent at a therapeutically effective amount.

These and other embodiments of the present invention will be better understood in relation to the figures, description, examples and claims that follow.

EXAMPLES

Example 1: Preparation of Delivery Devices Containing Hydrogels

Devices made of hydrogels were prepared as follows:

i. co-solvents, preservatives and excipients (such as glycerol, trisodium citrate, sodium benzoate, and potassium sorbate) were added to double distilled water and mixed at 22° C. until a clear solution was formed;

ii. pharmaceutically active agents were added;

iii. the solution was heated at a rate of 10-15° C./min up to a temperature of 85° C.-95° C.;

iv. polysaccharides were added under agitation at 5000-8000 rpm and the solution was heated at 85° C.-95° C. for about 2 to 3 min;

v. cross-linking agents: KCl and/or $CaCl_2$ and/or NaCl, were added;

vi. the pH of the solution was adjusted by an acid (such as lactic acid or citric acid);

vii. the solution was poured to molds and cooled for a few hours; and viii. the hydrogel formed was then de-casted, resulting in a hydrophilic hydrogel of the present invention.

Example 2: Hydrogel Compositions

Various hydrogel formulations were prepared according to the procedure described in Example 1.

TABLE 1

Hydrogel formulation #1 (designated "formulation V-94").

| Ingredients | w/w (%) | Role in formulation |
| --- | --- | --- |
| DI (deionized) Water | 81.9 | |
| Glycerol | 5.0 | co-solvent |
| carrageenan and locust bean gum mixture | 0.5 | polysaccharide |
| gellan gum low acyl | 1.0 | polysaccharide |
| gellan gum high acyl | 1.0 | polysaccharide |
| KCl (5%) | 5.0 | cross-linking agent |
| $CaCl_2$ (5%) | 5.0 | cross-linking agent |
| Citric acid | 0.15 | pH modifier |
| Trisodium citrate | 0.30 | stabilizer |
| Sodium benzoate | 0.05 | preservative |
| Potassium sorbate | 0.1 | preservative |

TABLE 2

Hydrogel formulation #2 (designated "formulation 97-2").

| Ingredients | w/w (%) | Role in formulation |
| --- | --- | --- |
| DI Water | 89.90 | |
| Glycerol | 5.0 | Co-solvent |
| carrageenan and locust bean gum mixture | 1.50 | polysaccharide |
| gellan gum low acyl | 1.00 | polysaccharide |
| gellan gum high acyl | 1.20 | polysaccharide |
| KCl | 0.30 | cross-linking agent |
| NaCl | 0.50 | cross-linking agent |
| Lactic acid | 0.20 | pH modifier |
| Sodium benzoate | 0.20 | preservative |
| Potassium sorbate | 0.20 | preservative |

TABLE 3

Hydrogel formulation #3 (designated "formulation V-94-11").

| Ingredients | w/w (%) | Role in formulation |
| --- | --- | --- |
| DI Water | 76.25 | |
| Glycerol | 5.0 | Co-solvent |
| carrageenan and locust bean gum mixture | 0.50 | polysaccharide |
| gellan gum low acyl | 1.00 | polysaccharide |
| gellan gum high acyl | 1.00 | polysaccharide |
| KCl (5%) | 5.00 | cross-linking agent |
| $CaCl_2$ (5%) | 5.00 | cross-linking agent |
| Trisodium citrate | 0.30 | stabilizer |
| Sodium benzoate | 0.05 | preservative |
| Potassium sorbate | 0.10 | preservative |
| Hyaluronic acid | 0.50 | moisturizer and humectant |
| Aloe vera Extract | 5.00 | soothing agent |
| Ascorbic acid | 0.30 | Vitamin C |

TABLE 4

Hydrogel formulation #4 (designated "formulation T-98-18-1").

| Ingredients | w/w (%) | Role in formulation |
| --- | --- | --- |
| DI Water | 94.90 | |
| carrageenan and locust bean gum mixture | 0.50 | polysaccharide |
| gellan gum low acyl | 2.00 | polysaccharide |
| gellan gum high acyl | 1.00 | polysaccharide |
| KCl | 0.50 | cross-linking agent |
| $CaCl_2$ | 0.50 | cross-linking agent |
| Citric acid | 0.15 | pH modifier |
| Trisodium citrate | 0.30 | stabilizer |
| Sodium benzoate | 0.05 | preservative |
| Potassium sorbate | 0.10 | preservative |

TABLE 5

Hydrogel formulation #5 (designated "formulation T-101-1").

| Ingredients | w/w (%) | Role in formulation |
| --- | --- | --- |
| DI Water | 90.15 | |
| Glycerol | 5.00 | Co-solvent |
| carrageenan and locust bean gum mixture | 0.50 | polysaccharide |
| gellan gum low acyl | 2.00 | polysaccharide |
| gellan gum high acyl | 1.00 | polysaccharide |
| KCl | 0.30 | cross-linking agent |
| NaCl | 0.50 | cross-linking agent |
| Citric acid | 0.15 | pH modifier |
| Sodium benzoate | 0.20 | preservative |
| Potassium sorbate | 0.20 | preservative |

TABLE 6

Hydrogel formulation #6 (designated "T-120-1").

| Ingredients | w/w (%) | Role in formulation |
| --- | --- | --- |
| DI Water | 89.95 | |
| Glycerol | 5.00 | Co-solvent |
| carrageenan and locust bean gum mixture | 1.50 | polysaccharide |
| gellan gum low acyl | 1.00 | polysaccharide |
| gellan gum high acyl | 1.20 | polysaccharide |
| KCl | 0.30 | cross-linking agent |
| NaCl | 0.50 | cross-linking agent |

TABLE 6-continued

Hydrogel formulation #6 (designated "T-120-1").

| Ingredients | w/w (%) | Role in formulation |
|---|---|---|
| Citric acid | 0.15 | pH modifier |
| Sodium benzoate | 0.20 | preservative |
| Potassium sorbate | 0.20 | preservative |

Example 3: Preparation of Delivery Devices Containing Oil-in-Water Formulations Devices made of gels which were formed from oil-in-water (O/W) emulsions were prepared as follows:

i. co-solvents, preservatives and excipient (such as glycerol, trisodium citrate, sodium benzoate, and potassium sorbate) were added to double distilled water and mixed at 22° C. until a clear solution was formed;

ii. the solution was heated at a rate of 10-15° C./min to a temperature of 85° C.-95° C.;

iii. polysaccharides were added under agitation at 5000-8000 rpm and under heating at 85° C.-95° C. until full dissolution was achieved;

iv. surfactants (such as polysorbate 80) were added under agitation at 5000-8000 rpm;

v. oil (containing one or more hydrophobic beneficial ingredients) was added under agitation at 5000-8000 rpm to produce an emulsion;

vi. the emulsion was heated at about 95° C. ("Cooking") for about 2-3 min;

vii. cross-linking agents (such as KCl and/or $CaCl_2$ and/or NaCl) were added;

viii. the pH of the emulsion was adjusted by an acid (such as citric acid or lactic acid);

ix. the emulsion was poured to molds and cooled for a few hours; and ix. the gel formed was then de-casted, resulting in a gel containing an oil-in-water emulsion prior to gelation.

Example 4: Oil-in-Water Gel Formulations

Various O/W gel formulations were prepared according to the procedure described in Example 3.

TABLE 7

Oil-in-water gel formulation #7 (designated "formulation 94.7 O/W" containing 10% oil).

| Ingredients | w/w (%) | Role in formulation |
|---|---|---|
| DI Water | 71.00 | |
| Glycerol | 5.00 | Co-solvent |
| carrageenan and locust bean gum mixture | 0.50 | polysaccharide |
| gellan gum low acyl | 1.20 | polysaccharide |
| gellan gum high acyl | 1.20 | polysaccharide |
| Polysorbate 80 | 0.50 | surfactant |
| Coconut oil | 10.00 | oil |
| KCl (5%) | 5.00 | cross-linking agent |
| $CaCl_2$ (5%) | 5.00 | cross-linking agent |
| Citric acid | 0.15 | pH modifier |
| Trisodium citrate | 0.30 | stabilizer |
| Sodium benzoate | 0.05 | preservative |
| Potassium sorbate | 0.10 | preservative |

TABLE 8

Oil-in-water gel formulation #8 (designated "94.7 O/W" containing 20% oil).

| Ingredients | w/w (%) | Role in formulation |
|---|---|---|
| DI Water | 61.00 | |
| Glycerol | 5.00 | Co-solvent |
| carrageenan and locust bean gum mixture | 0.50 | polysaccharide |
| gellan gum low acyl | 1.20 | polysaccharide |
| gellan gum high acyl | 1.20 | polysaccharide |
| Polysorbate 80 | 0.50 | surfactant |
| Coconut oil | 20.00 | oil |
| KCl (5%) | 5.00 | cross-linking agent |
| $CaCl_2$ (5%) | 5.00 | cross-linking agent |
| Citric acid | 0.15 | pH modifier |
| Trisodium citrate | 0.30 | stabilizer |
| Sodium benzoate | 0.05 | preservative |
| Potassium sorbate | 0.10 | preservative |

TABLE 9

Oil-in-water gel formulation #9 (designated "formulation T-120-9").

| Ingredients | w/w (%) | Role in formulation |
|---|---|---|
| DI Water | 77.90 | |
| Glycerol | 5.00 | Co-solvent |
| carrageenan and locust bean gum mixture | 1.50 | polysaccharide |
| gellan gum low acyl | 1.00 | polysaccharide |
| gellan gum high acyl | 1.20 | polysaccharide |
| Sucrose Distearate | 1.50 | Surfactant (Sucrose ester HLB = 6) |
| Sucrose Palmitate | 0.50 | Surfactant (Sucrose ester HLB = 16) |
| Coconut oil | 10.00 | oil |
| KCl | 0.30 | stabilizer |
| NaCl | 0.50 | cross-linking agent |
| Lactic acid | 0.20 | pH modifier |
| Sodium benzoate | 0.20 | preservative |
| Potassium sorbate | 0.20 | preservative |

TABLE 10

Oil-in-water gel formulation #10 (designated "formulation T-96-17" containing 20% oil).

| Ingredients | w/w (%) | Role in formulation |
|---|---|---|
| DI Water | 73.65 | |
| carrageenan and locust bean gum mixture | 3.00 | polysaccharide |
| gellan gum low acyl | 1.25 | polysaccharide |
| Polysorbate 80 | 0.50 | surfactant |
| Coconut oil | 20.00 | oil |
| KCl | 0.50 | cross-linking agent |
| $CaCl_2$ | 0.50 | cross-linking agent |
| Citric acid | 0.15 | pH modifier |
| Trisodium citrate | 0.30 | stabilizer |
| Sodium benzoate | 0.05 | preservative |
| Potassium sorbate | 0.10 | preservative |

TABLE 11

Oil-in-water gel formulation #11 (designated "formulation T-96-17" containing 30% oil).

| Ingredients | w/w (%) | Role in formulation |
|---|---|---|
| DI Water | 63.65 | |
| carrageenan and locust bean gum mixture | 3.00 | polysaccharide |
| gellan gum low acyl | 1.25 | polysaccharide |
| Polysorbate 80 | 0.50 | surfactant |
| Coconut oil | 30.00 | oil |
| KCl | 0.50 | cross-linking agent |
| CaCl$_2$ | 0.50 | cross-linking agent |
| Citric acid | 0.15 | pH modifier |
| Trisodium citrate | 0.30 | stabilizer |
| Sodium benzoate | 0.05 | preservative |
| Potassium sorbate | 0.10 | preservative |

TABLE 12

Oil-in-water gel formulation #12 (designated "formulation T-94-18" containing 32 mg THC and 3.2 mg CBD added during emulsion preparation).

| Ingredients | w/w (%) | Role in formulation |
|---|---|---|
| DI Water | 68.8 | |
| carrageenan and locust bean gum mixture | 0.50 | polysaccharide |
| gellan gum low acyl | 2.00 | polysaccharide |
| gellan gum high acyl | 1.00 | polysaccharide |
| Sucrose ester | 1.00 | Surfactant |
| Coconut oil | 16.00 | oil |
| CAN1 (32 mg THC and 3.2 mg CBD) | 0.08 | pharmaceutically acceptable agents |
| KCl (5%) | 5.00 | cross-linking agent |
| CaCl$_2$ (5%) | 5.00 | cross-linking agent |
| Citric acid | 0.15 | pH modifier |
| Trisodium citrate | 0.30 | stabilizer |
| Sodium benzoate | 0.05 | preservative |
| Potassium sorbate | 0.10 | preservative |

TABLE 13

Oil-in-water gel formulation #13 (designated "formulation T-98-18-2" containing 10% oil).

| Ingredients | w/w (%) | Role in formulation |
|---|---|---|
| DI Water | 84.40 | |
| carrageenan and locust bean gum mixture | 0.50 | polysaccharide |
| gellan gum low acyl | 2.00 | polysaccharide |
| gellan gum high acyl | 1.00 | polysaccharide |
| Polysorbate 80 | 0.50 | surfactant |
| Coconut oil | 10.00 | oil |
| KCl | 0.50 | cross-linking agent |
| CaCl$_2$ | 0.50 | cross-linking agent |
| Citric acid | 0.15 | pH modifier |
| Trisodium citrate | 0.30 | stabilizer |
| Sodium benzoate | 0.05 | preservative |
| Potassium sorbate | 0.10 | preservative |

TABLE 14

Oil-in-water gel formulation #14 (designated "formulation T-101-2" containing 10% oil).

| Ingredients | w/w (%) | Role in formulation |
|---|---|---|
| DI Water | 79.65 | |
| Glycerol | 5.00 | Co-solvent |
| carrageenan and locust bean gum mixture | 0.50 | polysaccharide |
| gellan gum low acyl | 2.00 | polysaccharide |
| gellan gum high acyl | 1.00 | polysaccharide |
| Polysorbate 80 | 0.50 | surfactant |
| Coconut oil | 10.00 | oil |
| KCl | 0.30 | cross-linking agent |
| NaCl | 0.50 | cross-linking agent |
| Citric acid | 0.15 | pH modifier |
| Sodium benzoate | 0.20 | preservative |
| Potassium sorbate | 0.20 | preservative |

TABLE 15

Oil-in-water gel formulation #15 (designated "formulation T-120-2" containing 10% oil).

| Ingredients | w/w (%) | Role in formulation |
|---|---|---|
| DI Water | 79.45 | |
| Glycerol | 5.00 | Co-solvent |
| carrageenan and locust bean gum mixture | 1.50 | polysaccharide |
| gellan gum low acyl | 1.00 | polysaccharide |
| gellan gum high acyl | 1.20 | polysaccharide |
| Polysorbate 80 | 0.50 | surfactant |
| Coconut oil | 10.00 | oil |
| KCl | 0.30 | cross-linking agent |
| NaCl | 0.50 | cross-linking agent |
| Citric acid | 0.15 | pH modifier |
| Sodium benzoate | 0.20 | preservative |
| Potassium sorbate | 0.20 | preservative |

TABLE 16

Oil-in-water gel formulation #16 (designated "formulation T-120-5" containing 10% oil).

| Ingredients | w/w (%) | Role in formulation |
|---|---|---|
| DI Water | 79.45 | |
| Glycerol | 5.00 | Co-solvent |
| carrageenan and locust bean gum mixture | 1.50 | polysaccharide |
| gellan gum low acyl | 1.00 | polysaccharide |
| gellan gum high acyl | 1.20 | polysaccharide |
| Polysorbate 80 | 0.50 | surfactant |
| Coconut oil | 10.00 | oil |
| KCl | 0.30 | cross-linking agent |
| NaCl | 0.50 | cross-linking agent |
| Lactic acid | 0.15 | pH modifier |
| Sodium benzoate | 0.20 | preservative |
| Potassium sorbate | 0.20 | preservative |

Example 5: Mechanical Properties of Formulation 97-2

The effect of heating the formulations before solidification/gel formation on the mechanical properties of the hydrogels was determined.

To that end, samples of the formulation designated 97-2 (Table 2) were maintained at 80° C. for 0-180 minutes prior to pouring to molds and gel formation (Example 1). After de-casting the hydrogels from the molds, cylindrical samples were cut from the hydrogels and subjected to mechanical compression tests using Instron 3345 Tester equipped with a 100 N load cell at a crosshead speed of 2 mm/min. The diameter and height of the cylindrical samples were measured using a digital Caliper (0-150 mm). In order to assess the hydrogel elasticity, each sample was consecutively compressed (three times). The compression test was performed at 22° C.

Figure 2:
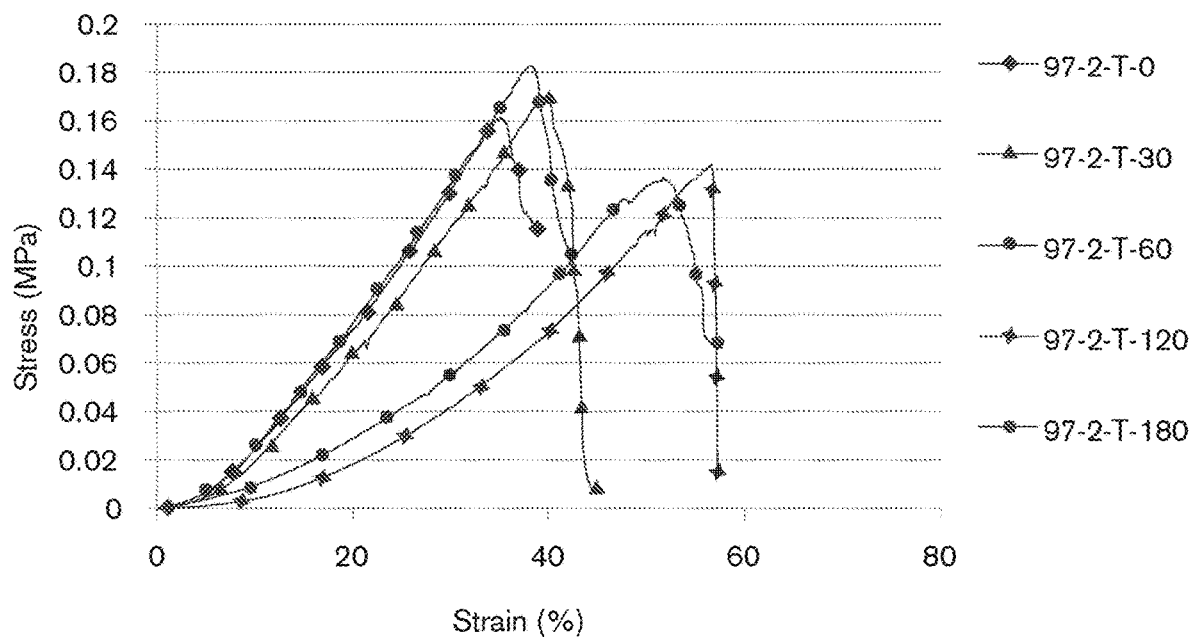
FIG. 2 shows the compression stress/strain curve of hydrogels produced from the formulation designated 97-2. The formulation was maintained at 80° C. for the indicated time periods before pouring into molds, and the gels formed were subjected to the compression test.

Compressive stress-strain curves for the hydrogel samples of formulation 97-2 are presented in FIG. 2, and the Young's modulus was determined from the linear slope of the low strain region (Table 17).

As shown in FIG. 2 and Table 17, maintaining the 97-2 formulation at 80° C. for 0 to 60 minutes prior to pouring into molds resulted in the formation of hydrogels having Young's modulus of about 0.53-0.55 MPa, while maintaining the 97-2 formulation at 80° C. for 120-180 minutes resulted in the formation of hydrogels having lower Young's modulus, i.e., about 0.27 MPa. These results indicate that maintaining the hydrophilic formulations at 80° C. for few hours prior to pouring to molds and solidification does not impair the mechanical properties of the hydrogels. Even more so, maintaining the hydrophilic formulations at 80° C. for few hours prior to pouring into molds brings about the formation of more flexible and elastic hydrogels.

TABLE 17

Young's modulus values of hydrogels produced from the formulation designated 97-2 after heating the formulation prior to solidification for various time periods.

| Formulation | Young's Modulus (MPa) |
|---|---|
| Formulation 97-2, time 0 | 0.5340 |
| Formulation 97-2, time 30 min | 0.53169 |
| Formulation 97-2, time 60 min | 0.55389 |
| Formulation 97-2, time 120 min | 0.27273 |
| Formulation 97-2, time 180 min | 0.27342 |

Example 6: Effect of Various Amounts of Oil and Effect of Storage of Gel on the Mechanical Properties of the Gels The aim of this study was to evaluate the stress at break and Young's modulus of gels produced from the formulation designated T-96-17 having various amounts of coconut oil: 0 wt %, 10 wt %, 20 wt % (Table 10), and 30 wt % (Table 11). The compression tests were performed on gels 24 hours after gel production or one week after gel production as described in Example 5 herein above.

Compression Tests in Gels 24 Hrs after Gel Production

Figure 3A:
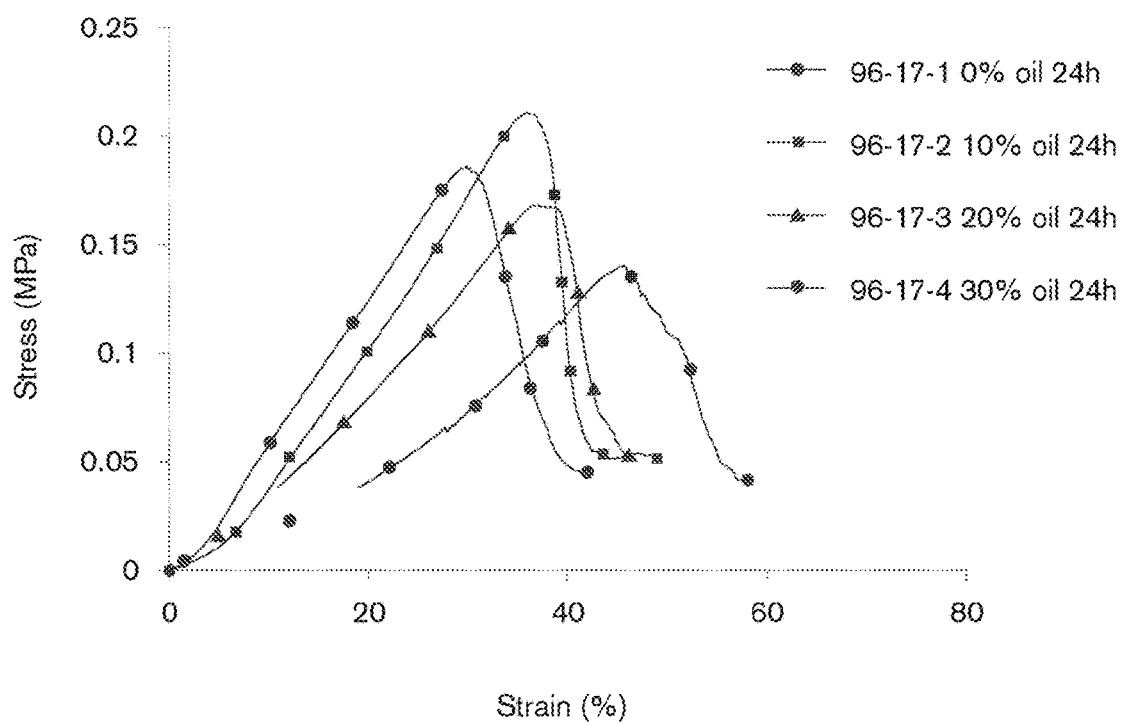
FIGS. 3A-B show the compression stress/strain curves of gels produced from the formulation designated T-96-17 containing increasing amounts of coconut oil.

Compression stress-strain curves are shown in FIG. 3A. Young's modulus values were determined from the linear slope of the low strain region of the stress-strain curves and were found to be 0.6925 MPa, 0.6272 MPa, 0.4863 MPa, and 0.2644 MPa for the gels having 0 wt %, 10 wt %, 20 wt %, and 30 wt % oil, respectively (Table 18).

TABLE 18

Young's modulus values of hydrogels produced from formulation 96-17 containing increasing amounts of oil measured 24 hours or one week after gel production.

| Formulation | Young's modulus (MPa) 24 hrs after production | Young's modulus (MPa) 1 week after production |
|---|---|---|
| Formulation 96-17 0% oil | 0.6925 | 0.648 |
| Formulation 96-17 10% oil | 0.6272 | 0.550 |

TABLE 18-continued

Young's modulus values of hydrogels produced from formulation 96-17 containing increasing amounts of oil measured 24 hours or one week after gel production.

| Formulation | Young's modulus (MPa) 24 hrs after production | Young's modulus (MPa) 1 week after production |
|---|---|---|
| Formulation 96-17 20% oil | 0.4863 | 0.454 |
| Formulation 96-17 30% oil | 0.2644 | 0.2534 |

These results indicate that increasing the amount of oil in the formulation results in decreasing Young's modulus of the gels, thus improving gel elasticity.

Compression Tests in Gels One Week after Gel Production

Figure 3B:
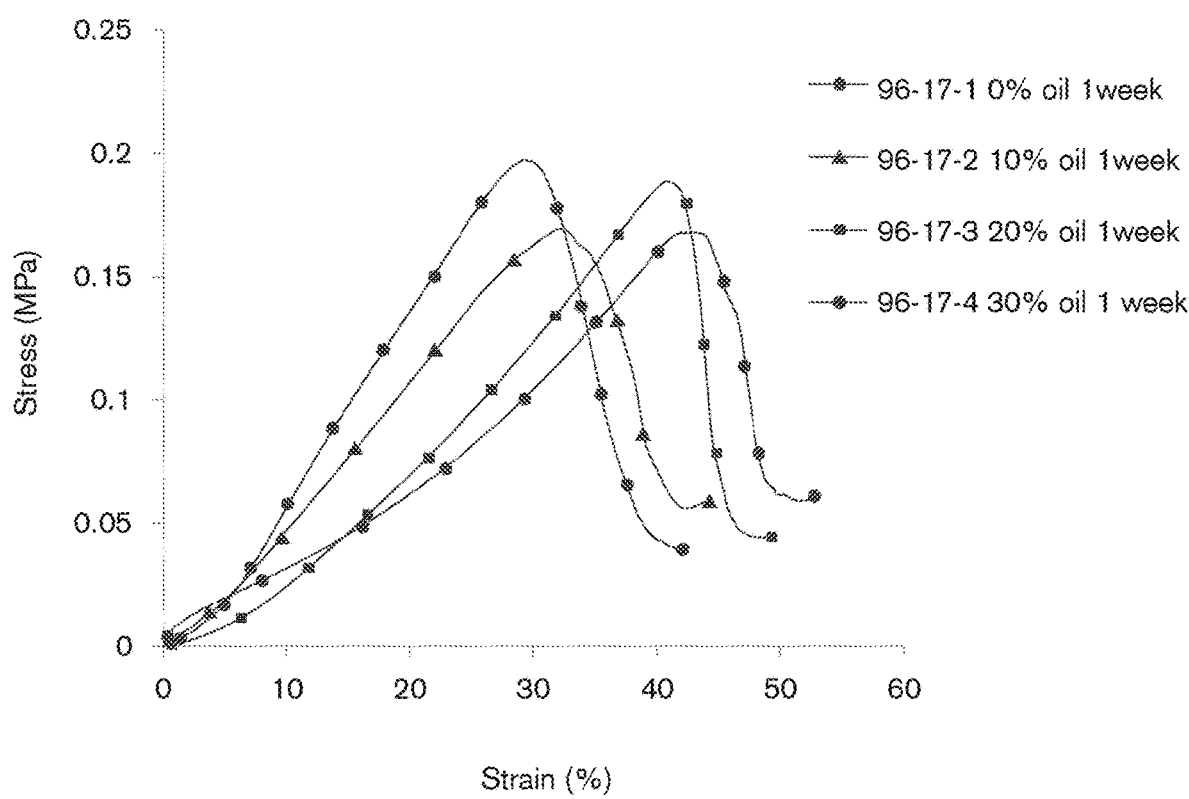

Compression stress-strain curves are shown in FIG. 3B. Young's modulus values were determined from the linear slope of the low strain region of the stress-strain curves and were found to be 0.648 MPa, 0.5502 MPa, 0.454 MPa, and 0.2534 MPa for the gels having 0 wt %, 10 wt %, 20 wt %, and 30 wt % oil, respectively (Table 18).

These results indicate that increasing the amount of oil in the formulation results in decreasing Young's modulus of the gels, thus improving gel elasticity.

In addition, these results indicate that storage of the gels, whether hydrogels or gels containing O/W emulsion prior to gelation, for several days after gel production improves gel elasticity (Table 18).

Example 7: Effect of the Polysaccharide Content and Composition on the Mechanical Properties of the Gels The aim of this study was to evaluate the effect of the polysaccharide content and composition on the stress at break and Young's modulus of gels.

A compressive stress-strain test with a formulation designated T-96-17-1 (which is similar to formulation T-96-17 but is devoid of oil) and with a formulation designated T-98-18-1 (which is similar to formulation T-98-18-2 but is devoid of oil) was performed 24 hours or one week after gel production as described in Example 5 and the Young's modulus values were determined. It is to be noted that the two hydrogel formulations: T-96-17 and T-98-18-1 were different from each other in the content and composition of the polysaccharides.

As shown in Table 19, the difference in polysaccharide content and composition between these two hydrogels did not affect their Young's modulus as measured 24 hours after gel production, indicating that these two formulations produced hydrogels with essentially similar elasticity.

TABLE 19

Young's modulus values for formulations T-96-17 and T-98-18-1.

| Sample | Young's modulus (MPa) 24 hr after production | Young's modulus (MPa) 1 week after production |
|---|---|---|
| Formulation 96-17-1, 0% oil | 0.691 MPa | NA |
| Formulation 98-18-1, 0% oil | 0.6925 MPa | 0.648 MPa |

Example 8: Effect of Increasing Amounts of Oil in Formulation 98-18 and Time after Gel Production on the Mechanical Properties of the Gels The aim of this study was to evaluate the stress at break and Young's modulus of the formulation designated T-98-18 containing increasing amounts of coconut oil (Tables 4 and 13). To this end, mechanical compression tests of cylindrical samples were performed 24 hrs and 1 week after gel production as described in Example 5. The Young's modulus values were determined and are presented in Table 20.

As shown in Table 20, as the amount of oil in the formulation increased, Young's modulus values of the gels, containing O/W emulsion prior to gelation, decreased, indicating that the gels are more elastic when the oil content is higher. Also, storage of the gels for one week does not impair the elasticity of the gels.

TABLE 20

Young's modulus values of gel produced from the formulation designated T-98-18 containing increasing amounts of oil.

| Formulation | Young's modulus (MPa) 24 hr after production | Young's modulus (MPa) 1 week after production |
|---|---|---|
| Formulation 98-18-1 with 0% oil | 0.691 MPa | 0.6520 |
| Formulation 98-18-2 with 10% oil | 0.665 MPa | 0.58315 |
| Formulation 98-18-3 with 20% oil | 0.548 MPa | NA |

Example 9: Effect of Glycerol on the Mechanical Properties of Formulation T-94-18

Figure 4:
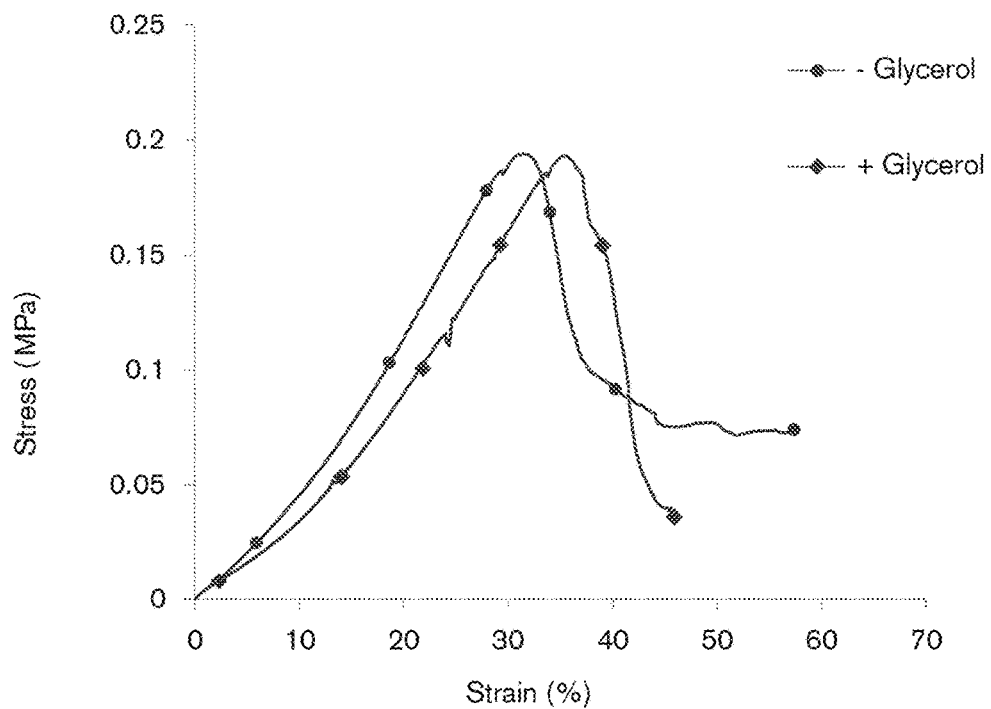
FIG. 4 shows the compression stress/strain curve of gels containing the oil-in-water emulsion formulation designated T-98-18 with and without glycerol.

The aim of this study was to evaluate the stress at break and Young's modulus of oil-in-water gels produced from the formulation designated T-94-18 in the absence or presence of 5 wt % glycerol in the formulation. To this end, mechanical compression tests of cylindrical samples of the gels were performed as described in Example 5 and the stress-strain curves are presented in FIG. 4. Young's modulus values were determined from the linear slope of the low strain region (FIG. 4) and were as follows: 0.5323 MPa and 0.5787 MPa for T-98-18 with glycerol and T-98-18 without glycerol, respectively.

These results indicate that glycerol does not have a significant effect on the elasticity of the gels.

Example 10: Impregnation of THC and CBD in Gels

Hydrogels or O/W gels were impregnated with an oil mixture containing the cannabinoids tetrahydrocannabinol (THC) and cannabidiol (CBD), and the amount of THC and CBD released from the gels was evaluated by HPLC.

A mixture of coconut oil and *cannabis* extract oil which contains THC and CBD was prepared in a ratio of 3:1 (w/w), respectively. The oil mixture contained 100 mg THC and 14 mg CBD.

Impregnation was performed as follows:
(a) a hydrogel or an O/W gel were prepared as described in Example 1 and Example 3, respectively;
(b) after solidification the gel was removed from the device mold;
(c) oil mixture containing coconut oil and *cannabis* extract oil which contains 100 mg THC and 14 mg CBD was added to the inner bottom of the mold, and the gels were impregnated with the oil mixture for 24 hrs at 37° C. followed by 6 days at 22° C.

Extraction and measurement of THC and CBD were performed as follows:
(a) the impregnated gel was removed from the mold and sealed in a plastic bag containing 100 ml of saline solution (pH of about 4.5);
(b) the sealed bag was vigorously agitated for 15 min;
(c) the gel was removed from the bag and the saline solution was collected;
(d) 100 ml of methanol were added to the bag which was sealed and sonicated at 40° C. for 15 min;
(e) the methanol was collected and mixed with the saline solution to form a homogenous solution; and
(f) the solution of (e) was filtered through 0.22 micron mesh and was subjected to HPLC.

Example 11: Release of THC and CBD from Gels Impregnated with THC and CBD

The following formulations: T-120-7, T-120-8, T-120-9, and T-120-10, T-120-11, and T-120-13 containing increasing amounts of coconut oil and different surfactants were used for the preparation of gels. The gels were impregnated with the oil mixture containing THC and CBD, and the amount of THC and CBD released from the gels was measured as described in Example 12. The amounts of THC and CBD released from the gels are presented in Table 21.

As shown in Table 21, the composition and the amount of the surfactants affected the release of THC and CBD from the gels. The combination of the surfactants: sucrose palmitate and sucrose distearate was found to improve the release of THC from the gel as compared to polysorbate 80 (Table 21).

Also, increasing the amount of oil in the formulations which contain the same amount and composition of the surfactants improved the release of THC from the gel. These results indicated that the formulation designated T-120-9 which contained 10% w/w coconut oil and a mixture of sucrose palmitate and sucrose distearate released higher amounts of THC compared to formulations which contained lower amounts of oil and polysorbate 80.

TABLE 21

Release of THC and CBD from gels produced from formulation T-120, the gels impregnated with THC and CBD oil mixture.

| Formulation | Coconut oil (wt %) | Surfactant (wt %) | CBD release (mg) | THC release (mg) |
|---|---|---|---|---|
| T-120-11 | 2% | 1% Polysorbate 80 | 0.41722 | 3.74668 |
| T-120-13 | 2% | 0.5% Sucrose Palmitate + 1.5% Sucrose Distearate | 0.43178 | 6.86756 |
| T-120-7 | 10% | 1% Polysorbate 80 | 0.279 | 18.01 |
| T-120-8 | 10% | 1% Sucrose Palmitate | 0.428 | 16.93 |
| T-120-9 | 10% | 0.5% Sucrose Palmitate + 1.5% Sucrose Distearate | 0.287 | 24.58 |
| T-120-10 | 20% | 1% Polysorbate 80 | 0.353 | 17.762 |

Next, the effect of the polysaccharide composition and amount in the formulations on the release of various cannabinoids from the gels was evaluated. The formulations used for the gel preparation were as follows: T-101-1 without oil (Table 5), T-101-2 with 10% oil (Table 14), T-120-1 without Oil (Table 6), and T-120-2 with 10% oil (Table 15).

The impregnation step was performed using *cannabis* oil extract containing the following cannabinoids: Cannabidiolic Acid (CBDA), Tetrahydrocannabinolic acid (THCA-A), CBD, Cannabigerol (CBG), Cannabinol (CBN), -trans-Δ9-tetrahydrocannabinol (THC-9), -trans-Δ8-tetrahydrocannabinol (THC-8), and Cannabichromene (CBC).

Figure 5:
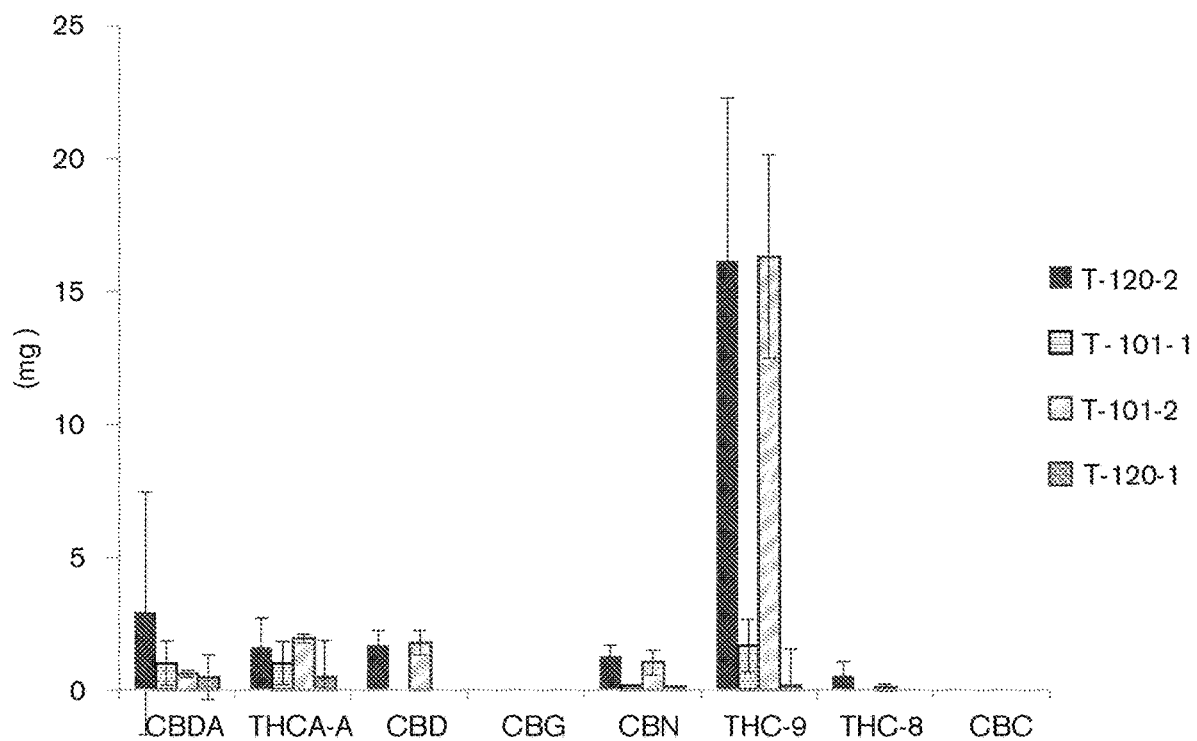
FIG. 5 depicts the release results of various cannabinoids from gel formulation designated T-100-1, T-101-2, T-120-1, and T-120-2.

The release of the various cannabinoids is presented in FIG. 5. As shown in FIG. 5, both formulations that contained 10% oil, namely T-101-2 and T-120-2, released THC-9 from the gels at significantly higher levels than the formulations devoid of oil, namely T-101-1 and T-120-1. In addition, the amount and composition of the polysaccharides did not have a significant effect on the release of THC-9 from the gels (FIG. 5).

Next, the release of various cannabinoids was determined from either hydrogels prepared from the formulation designated 97-2 (Table 2) or from O/W gels prepared from the formulation designated T-120-5 (Table 16). The experiment was repeated twice, and the results are summarized in Table 22.

As shown in Table 22, the release of cannabinoids, which are hydrophobic agents, was higher from O/W gels than from hydrogels.

TABLE 22

Release of cannabinoids from gels prepared from the formulations 97-2 and T-120-5.

| Formulation | CBDA (mg) | THCA-A (mg) | CBD (mg) | CBG (mg) | CBN (mg) | THC-9 (mg) | THC-8 (mg) | CBC (mg) |
|---|---|---|---|---|---|---|---|---|
| 97-2-X1 | 0.376 | 0.27115 | 0 | 0.078 | 0 | 0.4208 | 0 | 0 |
| 97-2-X1 | 0.3193 | 0.26705 | 0 | 0.07935 | 0 | 0.4676 | 0 | 0 |
| T-120-5 | 0.3975 | 0.3159 | 0.1745 | 0.30105 | 0 | 3.90495 | 0 | 0 |
| T-120-5 | 0.3418 | 0.31095 | 0.1206 | 0.18265 | 0 | 2.15665 | 0 | 0 |

Example 12: Release of Niacin from Hydrogels Impregnated with Niacin or Contained Niacin in the Formulation This study aimed at evaluating the release of niacin from hydrogels prepared in the presence of niacin or from hydrogels impregnated with a niacin solution.

To this end, the formulation designated 97.4 (Table 23) which contained 3% (w/w) niacin was used for the preparation of the hydrogel as detailed in Example 1 herein above.

TABLE 23

Hydrogel formulation #17 (designated "formulation 97.4" containing 3% w/w niacin).

| Compound | w/w (%) | Role in formulation |
|---|---|---|
| DI Water | 86.9 | |
| carrageenan and locust bean gum mixture | 1.50 | polysaccharide |
| gellan gum low acyl | 1.00 | polysaccharide |
| gellan gum high acyl | 1.20 | polysaccharide |
| Glycerol | 5.00 | Co-solvent |
| NaCl | 0.50 | Cross-linking agent |
| KCl | 0.30 | Cross-linking agent |
| Sodium benzoate | 0.20 | preservative |
| Potassium sorbate | 0.20 | preservative |
| Lactic acid | 0.20 | pH modifier |
| Niacin | 3.00 | Active agent |

The formulation designated 97-X-2 (Table 24) was used for the preparation of the hydrogel.

TABLE 24

Hydrogel formulation #18 (designated "formulation 97-X-2").

| Compound | w/w (%) | Role in formulation |
|---|---|---|
| DI Water | 89.9 | |
| carrageenan and locust bean gum mixture | 1.50 | polysaccharide |
| gellan gum low acyl | 1.00 | polysaccharide |
| gellan gum high acyl | 1.20 | polysaccharide |
| Glycerol | 5.00 | Co-solvent |
| NaCl | 0.50 | Cross-linking agent |
| KCl | 0.30 | Cross-linking agent |
| Sodium benzoate | 0.20 | preservative |
| Potassium sorbate | 0.20 | preservative |
| Lactic acid | 0.20 | pH modifier |

The hydrogel produced from formulation 97-X-2 was impregnated overnight with a solution of 1M niacin, pH 4 at 40° C. At the end of the impregnation, 3% (w/w) niacin was absorbed to the hydrogel.

Determination of the amount of niacin released from the hydrogels was performed as follows: the hydrogels were soaked in 1 liter saline, pH 4.5 under continuous stirring at 37° C. Samples of the saline solution were removed and the amount of niacin released was determined at 262 nm using UV-visible double beam spectrophotometer (Agilent 8453) with 0.1 cm matched quartz cells.

Figure 6:
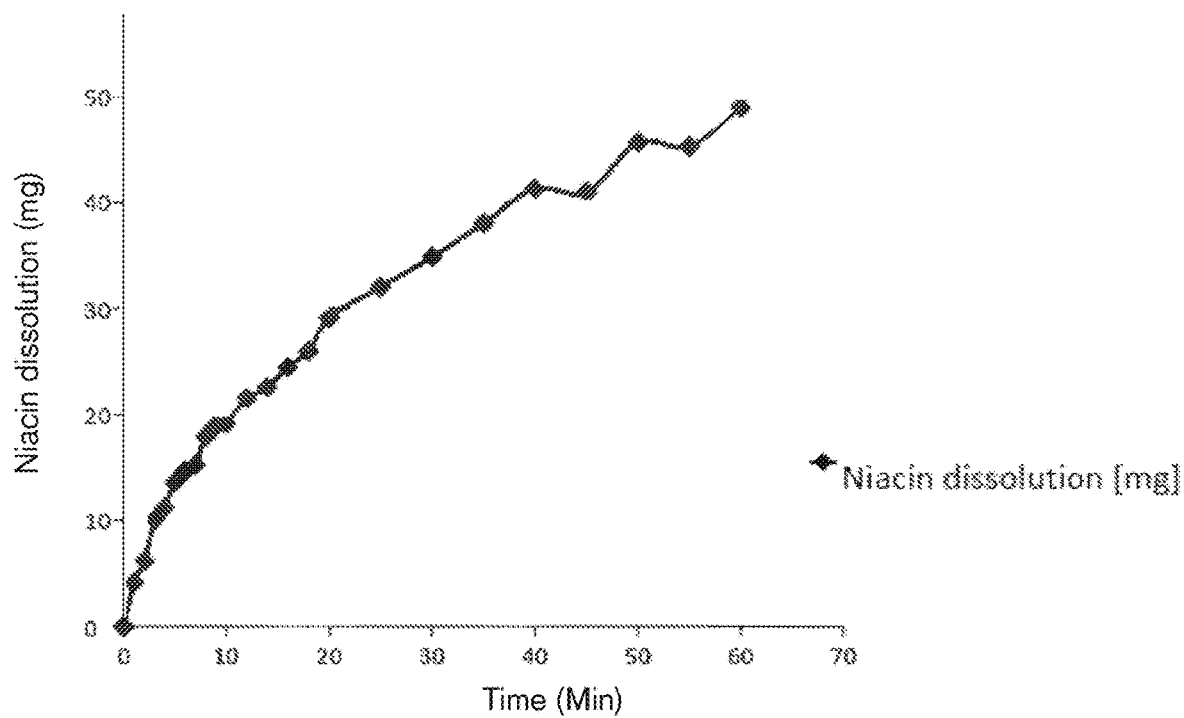
FIG. 6 depicts niacin dissolution over time from hydrogels impregnated in a niacin solution.
Figure 7:
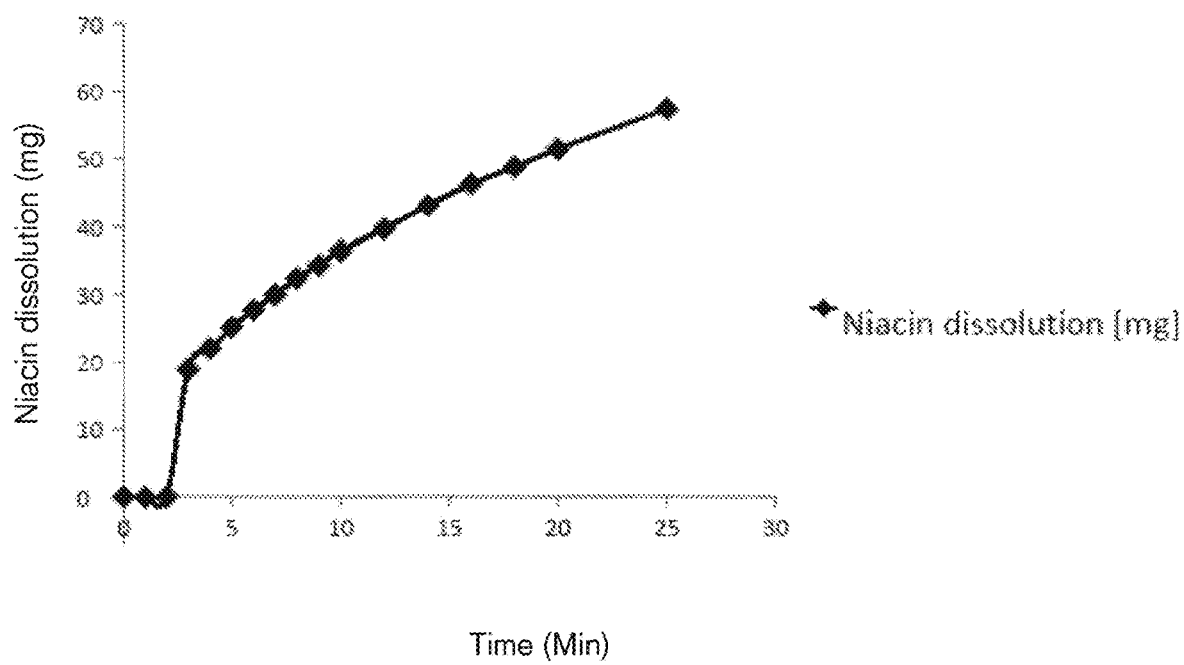
FIG. 7 depicts niacin dissolution over time from hydrogels containing niacin.

The release/dissolution of niacin from the hydrogel which was impregnated with niacin solution (formulation 97-X-2) is presented in FIG. 6. The release/dissolution of niacin from the hydrogel which was prepared in the presence of niacin in its formulation (formulation 97-4) is shown in FIG. 7. As shown in FIGS. 6 and 7, both hydrogels released niacin to the solution within few minutes, e.g., 10-30 minutes, indicating that the hydrogels/devices are capable of releasing dozens of mg of niacin to the external solution.

It will be appreciated by persons skilled in the art that the present invention is not limited by what has been particularly shown and described herein above. Rather the scope of the invention is defined by the claims that follow.

The invention claimed is:

1. . A delivery device adapted to mechanically dilate a pelvic anatomical canal of a human subject, the device comprising a composition comprising:
(a) a naturally occurring polysaccharide in an amount ranging from about 1% to about 5% by weight of the composition including low acyl gellan gum in an amount of at least 1% by weight of the composition;
(b) water in an amount of about 60% to about 88% by weight of the composition;
(c) a surfactant in an amount ranging from 0% to about 5% by weight of the composition;
(d) oil in an amount ranging from 0% to about 40% by weight of the composition;

(e) a pH modifying agent;
(f) a cross-linking agent; and
(g) a hydrophilic agent and/or a hydrophobic agent, each of the hydrophilic agent and/or the hydrophobic agent having a beneficial or therapeutic effect in the pelvic anatomical canal,
wherein the composition is formulated as a solid hydrogel in a shape of a cone having a first diameter and a second diameter the first diameter being larger than the second diameter, a length of about 120 mm to about 170 mm, a Young's modulus of about 100 KPa to about 1 MPa, and wherein the pH of the solid hydrogel ranges from about 3.5 to about 5.

2. The delivery device according to claim 1, wherein the naturally occurring polysaccharide is selected from the group consisting of locust bean gum, carrageenan, gellan gum, agar, gum karaya, gum Arabic, gum tragacanth, guar gum, konjac gum, pectin, xanthan gum, welan gum, native or modified starch, inulin, a cellulose derivative, chitin, chitosan, alginate, hyaluronic acid, and a combination thereof.

3. The delivery device according to claim 1, wherein the surfactant is selected from the group consisting of nonionic surfactants, anionic surfactants, cationic surfactants, and amphoteric surfactants.

4. The delivery device according to claim 1, wherein the oil is selected from the group consisting of vegetable oil, animal oil, and mineral oil.

5. The delivery device according to claim 1, wherein the cross-linking agent is selected from the group consisting of salts of monovalent cations, divalent cations, trivalent cations, quadrivalent cations, and a combination thereof.

6. The delivery device according to claim 1, wherein the amount of the cross-linking agent is up to about 10% by weight of the composition.

7. The delivery device according to claim 1, wherein the hydrophilic agent and/or the hydrophobic agent are selected from the group consisting of vitamins, hyaluronic acid, collagen, *cannabis* oils, cannabinoids, probiotics, plant extracts, and therapeutically active agents known to treat or affect a disease or disorder of an anatomical pelvic canal.

8. The delivery device according to claim 7, wherein the therapeutically active agent is selected from the group consisting of analgesic agent, antibacterial agents, antifungal agents, antiviral agents, anti-itch agents, and healing agents, or a combination thereof.

9. The delivery device according to claim 1, further comprising a pharmaceutically acceptable excipient selected from the group consisting of polar co-solvents, stabilizers, preservatives, and mixtures thereof.

10. The delivery device according to claim 1, wherein the cross-linking agent is in an amount of up to about 10% by weight of the composition and the composition optionally further comprises a polar co-solvent.

11. The delivery device according to claim 1, wherein the cross-linking agent is in an amount ranging from about 0.1% to about 5% by weight of the composition and the composition further comprises a polar co-solvent in an amount ranging from 0% to about 10% by weight of the composition.

12. The delivery device according to claim 1, wherein the oil is in an amount ranging from 0.1% to about 40% by weight of the composition; the cross-linking agent in an amount ranging from 0.1% to about 5% by weight of the composition; and the composition further comprises a polar co-solvent in an amount ranging from 0% to about 10% by weight of the composition.

13. The delivery device according to claim 1, wherein the anatomical pelvic canal is a vaginal canal and the pH of the composition ranges from about 3.8 to about 4.2.

14. A method for relieving or treating pain or discomfort of a woman having a disorder selected from the group consisting of vaginal stenosis, vaginal adhesions, vaginal contractions, and vaginal atrophy, the method comprising a step of inserting the delivery device according to claim 1 to a vaginal canal of the woman, thereby relieving or treating the pain or discomfort.

15. A method for treating female sexual dysfunction or improving female wellness comprising inserting the delivery device according to claim 1 to a vaginal canal of the woman, thereby treating female sexual dysfunction or improving female wellness.

16. The delivery device according to claim 1, wherein the first diameter is about 20 mm to about 60 mm, and the second diameter is about 10 mm to about 30 mm.

17. The delivery device according to claim 1, having a curvature or a bend so as to facilitate positioning and manipulation of the device during use.

18. The delivery device according to claim 1, wherein the solid hydrogel is prepared by adding the cross-linking agent at a temperature of about 85° C.-95° C.

* * * * *